United States Patent
Williams et al.

(10) Patent No.: US 11,670,153 B2
(45) Date of Patent: *Jun. 6, 2023

(54) SENSING PERIPHERAL HEURISTIC EVIDENCE, REINFORCEMENT, AND ENGAGEMENT SYSTEM

(71) Applicant: STATE FARM MUTUAL AUTOMOBILE INSURANCE COMPANY, Bloomington, IL (US)

(72) Inventors: Aaron Williams, Congerville, IL (US); Joseph Robert Brannan, Bloomington, IL (US); Christopher N. Kawakita, Normal, IL (US); Dana C. Hunt, Normal, IL (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/874,010

(22) Filed: Jul. 26, 2022

(65) Prior Publication Data

US 2022/0358825 A1 Nov. 10, 2022

Related U.S. Application Data

(63) Continuation of application No. 17/574,874, filed on Jan. 13, 2022, now Pat. No. 11,462,094, which is a
(Continued)

(51) Int. Cl.
*G08B 21/04* (2006.01)
*G16H 80/00* (2018.01)
*G06N 20/00* (2019.01)

(52) U.S. Cl.
CPC ......... *G08B 21/0484* (2013.01); *G06N 20/00* (2019.01); *G08B 21/0423* (2013.01);
(Continued)

(58) Field of Classification Search
CPC ............ G08B 21/0484; G08B 21/0423; G08B 21/0469; G08B 21/0476; G06N 20/00; G16H 80/00
(Continued)

(56) References Cited

U.S. PATENT DOCUMENTS

| 1,446,000 A | 2/1923 | Davis |
| 3,740,739 A | 6/1973 | Griffin et al. |

(Continued)

FOREIGN PATENT DOCUMENTS

| CN | 202865924 U | 4/2013 |
| IN | 201811043670 | 12/2018 |

(Continued)

OTHER PUBLICATIONS

"Elderly Alexa helps families care for their loved ones via voice", Perez, Sarah, techcrunch.com, May 14, 2017 (Year: 2017).
(Continued)

*Primary Examiner* — Hirdepal Singh
(74) *Attorney, Agent, or Firm* — Marshall, Gerstein & Borun LLP; Randall G. Rueth

(57) ABSTRACT

Systems and methods for identifying a condition associated with an individual in a home environment are provided. Sensors associated with the home environment detect data, which is captured and analyzed by a local or remote processor to identify the condition. In some instances, the sensors are configured to capture data indicative of electricity use by devices associated with the home environment, including, e.g., which devices are using electricity, what date/time electricity is used by each device, how long each device uses electricity, and/or the power source for the electricity used by each device. The processor analyzes the captured data to identify any abnormalities or anomalies, and, based upon any identified abnormalities or anomalies,
(Continued)

the processor determines a condition (e.g., a medical condition) associated with an individual in the home environment. The processor generates and transmits a notification indicating the condition associated with the individual to a caregiver of the individual.

23 Claims, 5 Drawing Sheets

Related U.S. Application Data continuation of application No. 17/077,785, filed on Oct. 22, 2020, now Pat. No. 11,423,758, which is a continuation of application No. 16/169,544, filed on Oct. 24, 2018, now Pat. No. 10,825,318.

(60) Provisional application No. 62/658,682, filed on Apr. 17, 2018, provisional application No. 62/654,975, filed on Apr. 9, 2018.

(52) U.S. Cl.
CPC ..... *G08B 21/0469* (2013.01); *G08B 21/0476* (2013.01); *G16H 80/00* (2018.01)

(58) Field of Classification Search
USPC ...................................................... 340/573.1
See application file for complete search history.

(56) References Cited

U.S. PATENT DOCUMENTS

| | | | |
|---|---|---|---|
| 3,817,161 A | 6/1974 | Koplon |
| 3,875,612 A | 4/1975 | Poitras |
| 4,066,072 A | 1/1978 | Cummins |
| 5,005,125 A | 4/1991 | Farrar et al. |
| 5,099,751 A | 3/1992 | Newman et al. |
| 5,128,859 A | 7/1992 | Carbone et al. |
| 5,553,609 A | 9/1996 | Chen et al. |
| 5,554,433 A | 9/1996 | Perrone et al. |
| 5,576,952 A | 11/1996 | Stutman et al. |
| 5,684,710 A | 11/1997 | Ehlers et al. |
| 5,884,289 A | 3/1999 | Anderson et al. |
| 5,903,426 A | 5/1999 | Ehling |
| 5,935,251 A | 8/1999 | Moore |
| 5,967,975 A | 10/1999 | Ridgeway |
| 6,023,762 A | 2/2000 | Dean et al. |
| 6,026,166 A | 2/2000 | Lebourgeois |
| 6,155,324 A | 12/2000 | Elliott et al. |
| 6,222,455 B1 | 4/2001 | Kaiser |
| 6,286,682 B1 | 9/2001 | Arbelles |
| 6,324,516 B1 | 11/2001 | Shults et al. |
| 6,351,698 B1 | 2/2002 | Kubota et al. |
| 6,428,475 B1 | 8/2002 | Shen |
| 6,466,921 B1 | 10/2002 | Cordery et al. |
| 6,526,807 B1 | 3/2003 | Doumit et al. |
| 6,535,855 B1 | 3/2003 | Cahill et al. |
| 6,554,183 B1 | 4/2003 | Sticha et al. |
| 6,611,206 B2 | 8/2003 | Eshelman et al. |
| 6,812,848 B2 | 11/2004 | Candela |
| 6,826,536 B1 | 11/2004 | Forman |
| 6,847,892 B2 * | 1/2005 | Zhou ............... G08C 17/02 |
| | | | 342/357.46 |
| 6,886,139 B2 | 4/2005 | Liu |
| 6,934,692 B1 | 8/2005 | Duncan |
| 6,954,758 B1 | 10/2005 | O'Flaherty |
| 7,030,767 B2 | 4/2006 | Candela |
| 7,091,865 B2 | 8/2006 | Cuddihy et al. |
| 7,154,399 B2 | 12/2006 | Cuddihy et al. |
| 7,194,416 B1 | 3/2007 | Provost et al. |
| 7,242,305 B2 | 7/2007 | Cuddihy et al. |
| 7,309,216 B1 | 12/2007 | Spadola et al. |
| 7,319,990 B1 | 1/2008 | Henty |
| 7,340,401 B1 | 3/2008 | Koenig et al. |
| 7,348,882 B2 | 3/2008 | Adamczyk et al. |
| 7,356,516 B2 | 4/2008 | Richey et al. |
| 7,395,219 B2 | 7/2008 | Strech |
| 7,397,346 B2 | 7/2008 | Helal et al. |
| 7,411,510 B1 | 8/2008 | Nixon |
| 7,467,094 B2 | 12/2008 | Rosenfeld et al. |
| 7,502,498 B2 | 3/2009 | Wen et al. |
| 7,562,121 B2 | 7/2009 | Berisford et al. |
| 7,586,418 B2 | 9/2009 | Cuddihy et al. |
| 7,598,856 B1 | 10/2009 | Nick et al. |
| 7,657,441 B2 | 2/2010 | Richey et al. |
| 7,715,036 B2 | 5/2010 | Silverbrook et al. |
| 7,733,224 B2 | 6/2010 | Tran |
| 7,809,587 B2 | 10/2010 | Dorai et al. |
| 7,813,822 B1 | 10/2010 | Hoffberg |
| 7,966,378 B2 | 6/2011 | Berisford et al. |
| 8,019,622 B2 | 9/2011 | Kaboff et al. |
| 8,031,079 B2 | 10/2011 | Kates |
| 8,041,636 B1 | 10/2011 | Hunter et al. |
| 8,050,665 B1 | 11/2011 | Orbach |
| 8,106,769 B1 | 1/2012 | Maroney et al. |
| 8,108,271 B1 | 1/2012 | Duncan et al. |
| 8,140,418 B1 | 3/2012 | Casey et al. |
| 8,185,191 B1 | 5/2012 | Shapiro et al. |
| 8,214,082 B2 | 7/2012 | Tsai et al. |
| 8,229,861 B1 | 7/2012 | Trandal et al. |
| 8,280,633 B1 | 10/2012 | Eldering et al. |
| 8,289,160 B1 | 10/2012 | Billman |
| 8,311,941 B2 | 11/2012 | Grant |
| 8,316,237 B1 | 11/2012 | Felsher et al. |
| 8,346,594 B2 | 1/2013 | Begeja et al. |
| 8,400,299 B1 | 3/2013 | Maroney et al. |
| 8,490,006 B1 | 7/2013 | Reeser et al. |
| 8,510,196 B1 | 8/2013 | Brandmaier et al. |
| 8,527,306 B1 | 9/2013 | Reeser et al. |
| 8,529,456 B2 | 9/2013 | Cobain |
| 8,533,144 B1 | 9/2013 | Reeser et al. |
| 8,571,993 B2 | 10/2013 | Kocher et al. |
| 8,595,034 B2 | 11/2013 | Bauer et al. |
| 8,596,293 B2 | 12/2013 | Mous et al. |
| 8,605,209 B2 | 12/2013 | Becker |
| 8,620,841 B1 | 12/2013 | Filson et al. |
| 8,621,097 B2 | 12/2013 | Venkatakrishnan et al. |
| 8,640,038 B1 | 1/2014 | Reeser et al. |
| 8,650,048 B1 | 2/2014 | Hopkins et al. |
| 8,665,084 B2 | 3/2014 | Shapiro et al. |
| 8,669,864 B1 | 3/2014 | Tedesco et al. |
| 8,670,998 B2 | 3/2014 | Bertha et al. |
| 8,675,920 B2 | 3/2014 | Hanson et al. |
| 8,682,952 B2 | 3/2014 | Kutzik et al. |
| 8,694,501 B1 | 4/2014 | Trandal et al. |
| 8,712,893 B1 | 4/2014 | Brandmaier et al. |
| 8,730,039 B1 | 5/2014 | Billman |
| 8,731,975 B2 | 5/2014 | English et al. |
| 8,744,901 B2 | 6/2014 | Begeja et al. |
| 8,749,381 B1 | 6/2014 | Maroney et al. |
| 8,803,690 B2 | 8/2014 | Junqua et al. |
| 8,856,383 B2 | 10/2014 | Beninato et al. |
| 8,868,616 B1 | 10/2014 | Otto et al. |
| 8,882,666 B1 | 11/2014 | Goldberg et al. |
| 8,890,680 B2 | 11/2014 | Reeser et al. |
| 8,917,186 B1 | 12/2014 | Grant |
| 8,929,853 B2 | 1/2015 | Butler |
| 8,965,327 B2 | 2/2015 | Davis et al. |
| 8,976,937 B2 | 3/2015 | Shapiro et al. |
| 9,049,168 B2 | 6/2015 | Jacob et al. |
| 9,057,746 B1 | 6/2015 | Houlette et al. |
| 9,082,072 B1 | 7/2015 | Wedding et al. |
| 9,111,349 B2 | 8/2015 | Szeliski et al. |
| 9,117,349 B2 | 8/2015 | Shapiro et al. |
| 9,142,119 B1 | 9/2015 | Grant |
| 9,152,737 B1 | 10/2015 | Micali et al. |
| 9,165,334 B2 | 10/2015 | Simon |
| 9,183,578 B1 | 11/2015 | Reeser et al. |
| 9,202,363 B1 | 12/2015 | Grant |
| 9,208,661 B2 | 12/2015 | Junqua et al. |
| 9,262,909 B1 | 2/2016 | Grant |
| 9,280,252 B1 | 3/2016 | Brandmaier et al. |
| 9,286,772 B2 | 3/2016 | Shapiro et al. |

(56) References Cited

U.S. PATENT DOCUMENTS

| | | |
|---|---|---|
| 9,297,150 B2 | 3/2016 | Klicpera |
| 9,344,330 B2 | 5/2016 | Jacob et al. |
| D764,461 S | 8/2016 | Romanoff et al. |
| 9,408,561 B2 | 8/2016 | Stone et al. |
| 9,424,606 B2 | 8/2016 | Wilson et al. |
| 9,424,737 B2 | 8/2016 | Bailey et al. |
| 9,429,925 B2 | 8/2016 | Wait |
| 9,443,195 B2 | 9/2016 | Micali et al. |
| 9,472,092 B1 | 10/2016 | Grant |
| 9,491,277 B2 | 11/2016 | Vincent |
| 9,536,052 B2 | 1/2017 | Amarasingham et al. |
| 9,589,441 B2 | 3/2017 | Shapiro et al. |
| 9,609,003 B1 | 3/2017 | Chmielewski et al. |
| 9,652,976 B2 | 5/2017 | Bruck et al. |
| 9,654,434 B2 | 5/2017 | Sone et al. |
| 9,665,892 B1 | 5/2017 | Reeser et al. |
| 9,666,060 B2 | 5/2017 | Reeser et al. |
| 9,699,529 B1 | 7/2017 | Petri et al. |
| 9,712,576 B1 | 7/2017 | Gill |
| 9,739,813 B2 | 8/2017 | Houlette et al. |
| 9,767,680 B1 | 9/2017 | Trundle |
| 9,786,158 B2 | 10/2017 | Beaver et al. |
| 9,798,979 B2 | 10/2017 | Fadell et al. |
| 9,798,993 B2 | 10/2017 | Payne et al. |
| 9,800,570 B1 | 10/2017 | Bleisch |
| 9,800,958 B1 | 10/2017 | Petri et al. |
| 9,812,001 B1 | 11/2017 | Grant |
| 9,824,397 B1 | 11/2017 | Patel et al. |
| 9,866,507 B2 | 1/2018 | Frenkel et al. |
| 9,888,371 B1 | 2/2018 | Jacob |
| 9,892,463 B1 | 2/2018 | Hakimi et al. |
| 9,898,168 B2 | 2/2018 | Shapiro et al. |
| 9,898,912 B1 | 2/2018 | Jordan et al. |
| 9,911,042 B1 | 3/2018 | Cardona et al. |
| 9,922,524 B2 | 3/2018 | Devdas et al. |
| 9,923,971 B2 | 3/2018 | Madey et al. |
| 9,942,630 B1 | 4/2018 | Petri et al. |
| 9,947,202 B1 | 4/2018 | Moon et al. |
| 9,978,033 B1 | 5/2018 | Payne et al. |
| 9,997,056 B2 | 6/2018 | Bleisch |
| 10,002,295 B1 | 6/2018 | Cardona et al. |
| 10,022,084 B2 | 7/2018 | Nonaka et al. |
| 10,042,341 B1 | 8/2018 | Jacob |
| 10,043,369 B2 | 8/2018 | Hopkins et al. |
| 10,047,974 B1 | 8/2018 | Riblet et al. |
| 10,055,793 B1 | 8/2018 | Call et al. |
| 10,055,803 B2 | 8/2018 | Orduna et al. |
| 10,057,664 B1 | 8/2018 | Moon et al. |
| 10,073,929 B2 | 9/2018 | Vaynriber et al. |
| 10,102,584 B1 | 10/2018 | Devereaux et al. |
| 10,102,585 B1 | 10/2018 | Bryant et al. |
| 10,107,708 B1 | 10/2018 | Schick et al. |
| 10,136,294 B2 | 11/2018 | Mehta et al. |
| 10,142,394 B2 | 11/2018 | Chmielewski et al. |
| 10,147,296 B2 | 12/2018 | Gregg |
| 10,176,705 B1 | 1/2019 | Grant |
| 10,181,160 B1 | 1/2019 | Hakimi-Boushehri et al. |
| 10,181,246 B1 | 1/2019 | Jackson |
| 10,186,134 B2 | 1/2019 | Moon et al. |
| 10,198,771 B1 | 2/2019 | Madigan et al. |
| 10,204,500 B2 | 2/2019 | Cullin et al. |
| 10,206,630 B2 | 2/2019 | Stone et al. |
| 10,217,068 B1 | 2/2019 | Davis et al. |
| 10,226,187 B2 | 3/2019 | Al-Ali et al. |
| 10,226,204 B2 | 3/2019 | Heaton et al. |
| 10,229,394 B1 | 3/2019 | Davis et al. |
| 10,244,294 B1 | 3/2019 | Moon et al. |
| 10,249,158 B1 | 4/2019 | Jordan et al. |
| 10,258,295 B2 | 4/2019 | Fountaine |
| 10,282,787 B1 | 5/2019 | Hakimi-Boushehri et al. |
| 10,282,788 B1 | 5/2019 | Jordan et al. |
| 10,282,961 B1 | 5/2019 | Jordan et al. |
| 10,295,431 B1 | 5/2019 | Schick et al. |
| 10,296,978 B1 | 5/2019 | Corder et al. |
| 10,297,138 B2 | 5/2019 | Reeser et al. |
| 10,298,735 B2 | 5/2019 | Preston et al. |
| 10,304,311 B2 | 5/2019 | Clark et al. |
| 10,304,313 B1 | 5/2019 | Moon et al. |
| 10,319,209 B2 | 6/2019 | Carlton-Foss |
| 10,323,860 B1 | 6/2019 | Riblet et al. |
| 10,325,471 B1 | 6/2019 | Victor |
| 10,325,473 B1 | 6/2019 | Moon et al. |
| 10,332,059 B2 | 6/2019 | Matsuoka et al. |
| 10,335,059 B2 | 7/2019 | Annegarn et al. |
| 10,346,811 B1 | 7/2019 | Jordan et al. |
| 10,353,359 B1 | 7/2019 | Jordan et al. |
| 10,356,303 B1 | 7/2019 | Jordan et al. |
| 10,380,692 B1 | 8/2019 | Parker et al. |
| 10,387,966 B1 | 8/2019 | Shah et al. |
| 10,388,135 B1 | 8/2019 | Jordan et al. |
| 10,412,169 B1 | 9/2019 | Madey et al. |
| 10,446,000 B2 | 10/2019 | Friar et al. |
| 10,446,007 B2 | 10/2019 | Kawazu et al. |
| 10,467,476 B1 | 11/2019 | Cardona et al. |
| 10,469,282 B1 | 11/2019 | Konrardy et al. |
| 10,475,141 B2 | 11/2019 | Mcintosh et al. |
| 10,480,825 B1 | 11/2019 | Riblet et al. |
| 10,482,746 B1 | 11/2019 | Moon et al. |
| 10,506,411 B1 | 12/2019 | Jacob |
| 10,506,990 B2 | 12/2019 | Lee et al. |
| 10,514,669 B1 | 12/2019 | Call et al. |
| 10,515,372 B1 | 12/2019 | Jordan et al. |
| 10,522,009 B1 | 12/2019 | Jordan et al. |
| 10,522,021 B1 | 12/2019 | Victor |
| 10,546,478 B1 | 1/2020 | Moon et al. |
| 10,547,918 B1 | 1/2020 | Moon et al. |
| 10,548,512 B2 | 2/2020 | Hausdorff et al. |
| 10,565,541 B2 | 2/2020 | Payne et al. |
| 10,573,146 B1 | 2/2020 | Jordan et al. |
| 10,573,149 B1 | 2/2020 | Jordan et al. |
| 10,579,028 B1 | 3/2020 | Jacob |
| 10,586,177 B1 | 3/2020 | Choueiter et al. |
| 10,607,295 B1 | 3/2020 | Hakimi-Boushehri et al. |
| 10,621,686 B2 | 4/2020 | Mazar et al. |
| 10,623,790 B2 | 4/2020 | Maddalena |
| 10,634,576 B1 | 4/2020 | Schick et al. |
| 10,664,922 B1 | 5/2020 | Madigan et al. |
| 10,679,292 B1 | 6/2020 | Call et al. |
| 10,685,402 B1 | 6/2020 | Bryant et al. |
| 10,699,346 B1 | 6/2020 | Corder et al. |
| 10,699,348 B1 | 6/2020 | Devereaux et al. |
| 10,726,494 B1 | 7/2020 | Shah et al. |
| 10,726,500 B1 | 7/2020 | Shah et al. |
| 10,733,671 B1 | 8/2020 | Hakimi-Boushehri et al. |
| 10,733,868 B2 | 8/2020 | Moon et al. |
| 10,735,829 B2 | 8/2020 | Petri et al. |
| 10,740,691 B2 | 8/2020 | Choueiter et al. |
| 10,741,033 B1 | 8/2020 | Jordan et al. |
| 10,750,252 B2 | 8/2020 | Petri et al. |
| 10,795,329 B1 | 10/2020 | Jordan et al. |
| 10,796,557 B2 | 10/2020 | Sundermeyer et al. |
| 10,802,477 B1 | 10/2020 | Konrardy et al. |
| 10,804,700 B2 | 10/2020 | Cohen et al. |
| 10,818,105 B1 | 10/2020 | Konrardy et al. |
| 10,823,458 B1 | 11/2020 | Riblet et al. |
| 10,824,971 B1 | 11/2020 | Davis et al. |
| 10,825,316 B1 | 11/2020 | Victor |
| 10,825,318 B1 | 11/2020 | Williams et al. |
| 10,825,320 B1 | 11/2020 | Moon et al. |
| 10,825,321 B2 | 11/2020 | Moon et al. |
| 10,832,225 B1 | 11/2020 | Davis et al. |
| 10,846,800 B1 | 11/2020 | Bryant et al. |
| 10,907,844 B2 | 2/2021 | Ribbich et al. |
| 10,922,756 B1 | 2/2021 | Call et al. |
| 10,922,948 B1 | 2/2021 | Moon et al. |
| 10,943,447 B1 | 3/2021 | Jordan et al. |
| 10,970,990 B1 | 4/2021 | Jacob |
| 10,990,069 B1 | 4/2021 | Jacob |
| 11,003,334 B1 | 5/2021 | Conway et al. |
| 11,004,320 B1 | 5/2021 | Jordan et al. |
| 11,015,997 B1 | 5/2021 | Schick et al. |
| 11,017,480 B2 | 5/2021 | Shah et al. |
| 11,042,131 B2 | 6/2021 | Strohmenger et al. |
| 11,042,137 B1 | 6/2021 | Call et al. |

(56) References Cited

U.S. PATENT DOCUMENTS

| | | |
|---|---|---|
| 11,042,938 B1 | 6/2021 | Robare |
| 11,042,942 B1 | 6/2021 | Hakimi-Boushehri et al. |
| 11,043,098 B1 | 6/2021 | Jordan et al. |
| 11,049,078 B1 | 6/2021 | Jordan et al. |
| 11,049,189 B2 | 6/2021 | Shah et al. |
| 11,074,659 B1 | 7/2021 | Hakimi-Boushehri et al. |
| 11,094,180 B1 | 8/2021 | Williams et al. |
| 11,100,594 B1 | 8/2021 | West et al. |
| 11,118,812 B1 | 9/2021 | Riblet et al. |
| 11,126,708 B2 | 9/2021 | Reimer |
| 11,138,861 B2 | 10/2021 | Blatt et al. |
| 11,164,257 B1 | 11/2021 | Devereaux et al. |
| 11,277,465 B2 | 3/2022 | Chmielewski et al. |
| 11,348,193 B1 | 5/2022 | Konrardy et al. |
| 2002/0040306 A1 | 4/2002 | Sugiyama et al. |
| 2002/0046047 A1 | 4/2002 | Budd |
| 2003/0023459 A1 | 1/2003 | Shipon |
| 2003/0144793 A1 | 7/2003 | Melaku et al. |
| 2004/0054789 A1 | 3/2004 | Breh et al. |
| 2004/0153346 A1 | 8/2004 | Grundel et al. |
| 2004/0153382 A1 | 8/2004 | Boccuzzi et al. |
| 2004/0177032 A1 | 9/2004 | Bradley et al. |
| 2004/0211228 A1 | 10/2004 | Nishio et al. |
| 2004/0220538 A1 | 11/2004 | Panopoulos |
| 2004/0249250 A1 | 12/2004 | McGee et al. |
| 2005/0030175 A1 | 2/2005 | Wolfe |
| 2005/0080520 A1 | 4/2005 | Kline et al. |
| 2005/0137465 A1 | 6/2005 | Cuddihy et al. |
| 2005/0139420 A1 | 6/2005 | Spoltore et al. |
| 2005/0143956 A1 | 6/2005 | Long et al. |
| 2005/0228245 A1 | 10/2005 | Quy |
| 2005/0251427 A1 | 11/2005 | Dorai et al. |
| 2005/0275527 A1 | 12/2005 | Kates |
| 2006/0001545 A1 | 1/2006 | Wolf |
| 2006/0033625 A1 | 2/2006 | Johnson et al. |
| 2006/0058612 A1 | 3/2006 | Dave et al. |
| 2006/0100912 A1 | 5/2006 | Kumar et al. |
| 2006/0154642 A1 | 7/2006 | Scannell |
| 2006/0184379 A1 | 8/2006 | Tan et al. |
| 2006/0205564 A1 | 9/2006 | Peterson |
| 2006/0271456 A1 | 11/2006 | Romain et al. |
| 2007/0186165 A1 | 8/2007 | Maislos et al. |
| 2008/0018474 A1 | 1/2008 | Bergman et al. |
| 2008/0019392 A1 | 1/2008 | Lee |
| 2008/0059351 A1 | 3/2008 | Richey et al. |
| 2008/0101160 A1 | 5/2008 | Besson |
| 2008/0154099 A1 | 6/2008 | Aspel et al. |
| 2008/0184272 A1 | 7/2008 | Brownewell |
| 2008/0201174 A1 | 8/2008 | Ramasubramanian et al. |
| 2008/0235629 A1 | 9/2008 | Porter et al. |
| 2008/0240379 A1 | 10/2008 | Maislos et al. |
| 2008/0285797 A1 | 11/2008 | Hammadou |
| 2008/0292151 A1 | 11/2008 | Kurtz et al. |
| 2008/0294462 A1 | 11/2008 | Nuhaan et al. |
| 2008/0301019 A1 | 12/2008 | Monk |
| 2009/0001891 A1 | 1/2009 | Patterson |
| 2009/0012373 A1 | 1/2009 | Raij et al. |
| 2009/0024420 A1 | 1/2009 | Winkler |
| 2009/0044595 A1 | 2/2009 | Vokey |
| 2009/0094129 A1 | 4/2009 | Rhodes et al. |
| 2009/0240170 A1 | 9/2009 | Rowley et al. |
| 2009/0243852 A1 | 10/2009 | Haupt et al. |
| 2009/0259581 A1 | 10/2009 | Horowitz et al. |
| 2009/0265193 A1 | 10/2009 | Collins et al. |
| 2009/0281393 A1 | 11/2009 | Smith |
| 2009/0326981 A1 | 12/2009 | Karkanias et al. |
| 2010/0027777 A1 | 2/2010 | Gupta et al. |
| 2010/0073840 A1 | 3/2010 | Hennessey, Jr. |
| 2010/0131416 A1 | 5/2010 | Means |
| 2010/0145164 A1 | 6/2010 | Howell |
| 2010/0191824 A1 | 7/2010 | Lindsay |
| 2010/0235285 A1 | 9/2010 | Hoffberg |
| 2010/0241465 A1 | 9/2010 | Amigo et al. |
| 2010/0286490 A1 | 11/2010 | Koverzin |
| 2010/0299217 A1 | 11/2010 | Hui |
| 2011/0003577 A1 | 1/2011 | Rogalski et al. |
| 2011/0021140 A1 | 1/2011 | Binier |
| 2011/0077875 A1 | 3/2011 | Tran et al. |
| 2011/0112660 A1 | 5/2011 | Bergmann et al. |
| 2011/0161117 A1 | 6/2011 | Busque et al. |
| 2011/0173122 A1 | 7/2011 | Singhal |
| 2011/0181422 A1 | 7/2011 | Tran |
| 2011/0201901 A1 | 8/2011 | Khanuja |
| 2011/0218827 A1 | 9/2011 | Kenefick et al. |
| 2011/0224501 A1 | 9/2011 | Hudsmith |
| 2011/0238564 A1 | 9/2011 | Lim et al. |
| 2011/0246123 A1 | 10/2011 | Dellostritto et al. |
| 2011/0251807 A1 | 10/2011 | Rada et al. |
| 2011/0276489 A1 | 11/2011 | Larkin |
| 2012/0016695 A1 | 1/2012 | Bernard et al. |
| 2012/0046973 A1 | 2/2012 | Eshleman et al. |
| 2012/0047072 A1 | 2/2012 | Larkin |
| 2012/0095846 A1 | 4/2012 | Leverant |
| 2012/0101855 A1 | 4/2012 | Collins et al. |
| 2012/0116820 A1 | 5/2012 | English et al. |
| 2012/0143754 A1 | 6/2012 | Patel |
| 2012/0166115 A1 | 6/2012 | Apostolakis |
| 2012/0188081 A1 | 7/2012 | Van Katwijk |
| 2012/0232935 A1 | 9/2012 | Voccola |
| 2012/0237908 A1 | 9/2012 | Fitzgerald et al. |
| 2012/0265586 A1 | 10/2012 | Mammone |
| 2012/0290333 A1 | 11/2012 | Birchall |
| 2012/0290482 A1 | 11/2012 | Atef et al. |
| 2013/0013513 A1 | 1/2013 | Ledbetter et al. |
| 2013/0030974 A1 | 1/2013 | Casey et al. |
| 2013/0049950 A1 | 2/2013 | Wohlert |
| 2013/0073299 A1 | 3/2013 | Warman et al. |
| 2013/0073306 A1 | 3/2013 | Shlain et al. |
| 2013/0073321 A1 | 3/2013 | Hofmann et al. |
| 2013/0082842 A1 | 4/2013 | Balazs et al. |
| 2013/0096960 A1 | 4/2013 | English et al. |
| 2013/0100268 A1 | 4/2013 | Mihailidis et al. |
| 2013/0104022 A1 | 4/2013 | Coon |
| 2013/0122849 A1 | 5/2013 | Doezema et al. |
| 2013/0143519 A1 | 6/2013 | Doezema |
| 2013/0144486 A1 | 6/2013 | Ricci |
| 2013/0147899 A1 | 6/2013 | Labhard |
| 2013/0159021 A1 | 6/2013 | Felsher |
| 2013/0166325 A1 | 6/2013 | Ganapathy et al. |
| 2013/0223405 A1 | 8/2013 | Kim et al. |
| 2013/0226624 A1 | 8/2013 | Blessman et al. |
| 2013/0234840 A1 | 9/2013 | Trundle et al. |
| 2013/0257626 A1 | 10/2013 | Masli et al. |
| 2013/0262155 A1 | 10/2013 | Hinkamp |
| 2013/0267795 A1 | 10/2013 | Cosentino et al. |
| 2013/0290013 A1 | 10/2013 | Forrester |
| 2013/0290033 A1 | 10/2013 | Reeser et al. |
| 2013/0304514 A1 | 11/2013 | Hyde et al. |
| 2014/0006284 A1 | 1/2014 | Faith et al. |
| 2014/0058854 A1 | 2/2014 | Ranganath et al. |
| 2014/0108031 A1 | 4/2014 | Ferrara |
| 2014/0122133 A1 | 5/2014 | Weisberg et al. |
| 2014/0136242 A1 | 5/2014 | Weekes et al. |
| 2014/0148733 A1 | 5/2014 | Stone et al. |
| 2014/0180723 A1 | 6/2014 | Cote et al. |
| 2014/0184408 A1 | 7/2014 | Herbst et al. |
| 2014/0201315 A1 | 7/2014 | Jacob et al. |
| 2014/0201844 A1 | 7/2014 | Buck |
| 2014/0207486 A1 | 7/2014 | Carty et al. |
| 2014/0222329 A1 | 8/2014 | Frey |
| 2014/0222469 A1 | 8/2014 | Stahl et al. |
| 2014/0229205 A1 | 8/2014 | Gibson |
| 2014/0238511 A1 | 8/2014 | Klicpera |
| 2014/0244997 A1 | 8/2014 | Goel et al. |
| 2014/0257851 A1 | 9/2014 | Walker et al. |
| 2014/0257871 A1 | 9/2014 | Christensen et al. |
| 2014/0266669 A1 | 9/2014 | Fadell et al. |
| 2014/0266717 A1 | 9/2014 | Warren et al. |
| 2014/0267263 A1 | 9/2014 | Beckwith et al. |
| 2014/0268353 A1 | 9/2014 | Fujimura et al. |
| 2014/0276549 A1 | 9/2014 | Osorio |
| 2014/0277939 A1 | 9/2014 | Ren et al. |
| 2014/0278571 A1 | 9/2014 | Mullen et al. |
| 2014/0303801 A1 | 10/2014 | Ahn et al. |

(56) References Cited

U.S. PATENT DOCUMENTS

| | | |
|---|---|---|
| 2014/0340216 A1 | 11/2014 | Puskarich |
| 2014/0340227 A1 | 11/2014 | Reed, Jr. |
| 2014/0358592 A1 | 12/2014 | Wedig et al. |
| 2014/0362213 A1 | 12/2014 | Tseng |
| 2014/0379156 A1 | 12/2014 | Kamel et al. |
| 2015/0002293 A1 | 1/2015 | Nepo |
| 2015/0032480 A1 | 1/2015 | Blackhurst et al. |
| 2015/0061859 A1 | 3/2015 | Matsuoka et al. |
| 2015/0094830 A1 | 4/2015 | Lipoma et al. |
| 2015/0116112 A1 | 4/2015 | Flinsenberg et al. |
| 2015/0134343 A1 | 5/2015 | Kluger et al. |
| 2015/0154712 A1 | 6/2015 | Cook |
| 2015/0154880 A1 | 6/2015 | Petito et al. |
| 2015/0160623 A1 | 6/2015 | Holley |
| 2015/0160636 A1 | 6/2015 | McCarthy et al. |
| 2015/0163412 A1 | 6/2015 | Holley et al. |
| 2015/0170288 A1 | 6/2015 | Harton et al. |
| 2015/0187016 A1 | 7/2015 | Adams et al. |
| 2015/0187019 A1 | 7/2015 | Fernandes et al. |
| 2015/0206249 A1 | 7/2015 | Fini |
| 2015/0244855 A1 | 8/2015 | Serra et al. |
| 2015/0287310 A1 | 10/2015 | Deiuliis et al. |
| 2015/0305690 A1 | 10/2015 | Tan et al. |
| 2015/0332407 A1 | 11/2015 | Wilson et al. |
| 2015/0347910 A1 | 12/2015 | Fadell et al. |
| 2015/0356701 A1 | 12/2015 | Gandy et al. |
| 2015/0364028 A1 | 12/2015 | Child et al. |
| 2016/0018226 A1 | 1/2016 | Plocher et al. |
| 2016/0042463 A1 | 2/2016 | Gillespie |
| 2016/0078744 A1 | 3/2016 | Gieck |
| 2016/0104250 A1 | 4/2016 | Allen et al. |
| 2016/0119424 A1 | 4/2016 | Kane et al. |
| 2016/0165387 A1 | 6/2016 | Nhu |
| 2016/0171864 A1 | 6/2016 | Ciaramelletti et al. |
| 2016/0174913 A1* | 6/2016 | Somanath ............ A61B 5/747 600/301 |
| 2016/0188829 A1 | 6/2016 | Southerland et al. |
| 2016/0225240 A1 | 8/2016 | Voddhi et al. |
| 2016/0259902 A1 | 9/2016 | Feldman et al. |
| 2016/0337829 A1 | 11/2016 | Fletcher et al. |
| 2016/0342767 A1 | 11/2016 | Narasimhan et al. |
| 2016/0360965 A1 | 12/2016 | Tran |
| 2016/0371620 A1 | 12/2016 | Nascenzi et al. |
| 2017/0124276 A1 | 5/2017 | Tee |
| 2017/0124277 A1 | 5/2017 | Shlagman |
| 2017/0147722 A1 | 5/2017 | Greenwood |
| 2017/0172465 A1 | 6/2017 | Osorio |
| 2017/0193164 A1 | 7/2017 | Simon et al. |
| 2017/0228109 A1 | 8/2017 | Zhang et al. |
| 2017/0262604 A1 | 9/2017 | Francois |
| 2017/0270260 A1 | 9/2017 | Shetty et al. |
| 2017/0277834 A1 | 9/2017 | Zipnick et al. |
| 2017/0304659 A1 | 10/2017 | Chen et al. |
| 2018/0000346 A1 | 1/2018 | Cronin |
| 2018/0000385 A1 | 1/2018 | Heaton et al. |
| 2018/0018864 A1 | 1/2018 | Baker |
| 2018/0032696 A1 | 2/2018 | Rome |
| 2018/0068081 A1 | 3/2018 | Salem |
| 2018/0075204 A1 | 3/2018 | Lee et al. |
| 2018/0122209 A1* | 5/2018 | Jefferson ............ A61B 5/0015 |
| 2018/0153477 A1 | 6/2018 | Nagale et al. |
| 2018/0160988 A1 | 6/2018 | Miller et al. |
| 2018/0211509 A1 | 7/2018 | Ramaci |
| 2018/0211724 A1 | 7/2018 | Wang |
| 2018/0228404 A1 | 8/2018 | Bhunia et al. |
| 2018/0228405 A1 | 8/2018 | Burwinkle et al. |
| 2018/0276710 A1 | 9/2018 | Tietzen et al. |
| 2018/0280245 A1 | 10/2018 | Khalid |
| 2018/0308569 A1 | 10/2018 | Luellen |
| 2018/0322947 A1 | 11/2018 | Potts et al. |
| 2018/0325470 A1 | 11/2018 | Fountaine |
| 2018/0342329 A1 | 11/2018 | Rufo et al. |
| 2018/0357386 A1 | 12/2018 | Sanjay-Gopal |
| 2018/0357879 A1 | 12/2018 | Negre et al. |
| 2018/0365957 A1* | 12/2018 | Wright ............ G08B 21/043 |
| 2019/0019379 A1 | 1/2019 | Beller et al. |
| 2019/0046039 A1* | 2/2019 | Ramesh ............ A61B 5/0024 |
| 2019/0069154 A1 | 2/2019 | Booth et al. |
| 2019/0083003 A1 | 3/2019 | Lee et al. |
| 2019/0099114 A1 | 4/2019 | Mouradian et al. |
| 2019/0108841 A1 | 4/2019 | Vergyri et al. |
| 2019/0122760 A1 | 4/2019 | Wang |
| 2019/0133445 A1 | 5/2019 | Eteminan et al. |
| 2019/0180879 A1 | 6/2019 | Jain et al. |
| 2019/0205675 A1 | 7/2019 | McGill |
| 2019/0206533 A1 | 7/2019 | Singh et al. |
| 2019/0228397 A1 | 7/2019 | Madden |
| 2019/0251520 A1 | 8/2019 | Bentley et al. |
| 2019/0279647 A1 | 9/2019 | Jones et al. |
| 2019/0287376 A1 | 9/2019 | Netscher et al. |
| 2019/0303760 A1 | 10/2019 | Kumar et al. |
| 2019/0320900 A1 | 10/2019 | Majmudar |
| 2019/0320945 A1 | 10/2019 | Johnson et al. |
| 2020/0019852 A1 | 1/2020 | Yoon et al. |
| 2020/0121544 A1 | 4/2020 | George et al. |
| 2020/0126670 A1 | 4/2020 | Bender et al. |
| 2020/0143655 A1 | 5/2020 | Gray et al. |
| 2020/0302549 A1 | 9/2020 | Jordan et al. |
| 2020/0327791 A1 | 10/2020 | Moon et al. |
| 2020/0334554 A1* | 10/2020 | Takahashi ............ G06F 11/3065 |
| 2020/0337651 A1 | 10/2020 | Kwan |
| 2021/0035432 A1 | 2/2021 | Moon et al. |
| 2021/0042843 A1 | 2/2021 | Bryant et al. |
| 2021/0158671 A1 | 5/2021 | Jordan et al. |
| 2021/0212576 A1* | 7/2021 | MacNeish ............ A61B 5/0816 |
| 2021/0307621 A1 | 10/2021 | Svenson et al. |

FOREIGN PATENT DOCUMENTS

| | | |
|---|---|---|
| JP | 2003-157357 A | 5/2003 |
| JP | 2014-142889 A | 8/2014 |
| KR | 10-2015-0129845 A | 11/2015 |
| WO | 2009/061936 A1 | 5/2009 |
| WO | 2011/133628 A1 | 10/2011 |
| WO | 2013/076721 A1 | 5/2013 |
| WO | 2014/159131 A2 | 10/2014 |
| WO | 2014/207558 A2 | 12/2014 |
| WO | 2016/081511 A2 | 5/2016 |
| WO | 2019/086849 A1 | 5/2019 |
| WO | 2020/010217 A1 | 1/2020 |

OTHER PUBLICATIONS

"How to use Alexa Care Hub to help monitor and contact older relatives or friends", Dave Johnson, Business Insider, Jan. 14, 2021, https://www.businessinsider.com/how-to-use-alexa-care-hub.

Amazons Care Hub will see success due to swelling interest in aging at home "and boosted smart speaker adoption", Zoe LaRock, Nov. 13, 2020, https://www.businessinsider.com/amazon-care-hub-will-succeed-amid-growing-smart-speaker-adoption-2020-11.

Final Office Action, U.S. Appl. No. 17/574,874, dated May 18, 2022.

Gurley, The Accuracy Of Self-Reported Data Of An Aging Population Using A Telehealth System In A Retirement Community Setting Based On The Users Age, Gender, Employment Status And Computer Experience, Dissertation, University of Maryland, Baltimore (2016).

Knutsen, Confusion about causation in insurance: solutions for catastrophic losses, Ala. L. Rev., 5:957-1023 (2010).

Michael E. Porter, "How Smart, Connected Products Are Transforming Competition", Harvard Business Review, Nov. 2014 (Year: 2014).

Non-Final Office Action, U.S. Appl. No. 17/574,874, dated Apr. 8, 2022, 17 pages.

Núñez-Marcos et al., Vision-Based Fall Detection with Convolutional Neural Networks, Wir. Comm. Mob. Comp., 2017(9474806):16 (2017).

System for Loss Prevention, IP.com, published Nov. 8, 2008.

The Accuracy Of Self-Reported Data Of An Aging Population Using A Telehealth System In A Retirement Community Setting

(56) References Cited

OTHER PUBLICATIONS

Based On The Users Age, Gender, Employment Status And Computer Experience, Gurley, Kelley Anne. University of Maryland, Baltimore.
U.S. Appl. No. 14/692,864, Final Office Action, dated Nov. 8, 2017.
U.S. Appl. No. 14/692,864, Non final Office Action, dated May 24, 2018.
U.S. Appl. No. 14/692,943, Non final Office Action, dated Sep. 12, 2017.
U.S. Appl. No. 14/692,943, Notice of Allowance, dated May 1, 2018.
U.S. Appl. No. 14/692,946, Final Office Action, dated Oct. 30, 2017.
U.S. Appl. No. 14/692,946, Nonfinal Office Action, dated Apr. 4, 2017.
U.S. Appl. No. 14/692,946, Nonfinal Office Action, dated Apr. 6, 2018.
U.S. Appl. No. 14/692,953, Final Office Action, dated Apr. 27, 2018.
U.S. Appl. No. 14/692,953, Nonfinal Office Action, dated Sep. 19, 2017.
U.S. Appl. No. 14/692,961, Final Office Action, dated Jun. 20, 2018.
U.S. Appl. No. 14/692,961, Final Office Action, dated Sep. 1, 2017.
U.S. Appl. No. 14/692,961, Nonfinal Office Action, dated Apr. 14, 2017.
U.S. Appl. No. 14/692,961, Nonfinal Office Action, dated Dec. 28, 2017.
U.S. Appl. No. 14/693,021, Final Office Action, dated Jan. 25, 2018.
U.S. Appl. No. 14/693,021, Nonfinal Office Action, dated Jun. 30, 2017.
U.S. Appl. No. 14/693,032, Final Office Action, dated Mar. 22, 2018.
U.S. Appl. No. 14/693,032, Nonfinal Office Action, dated Sep. 7, 2017.
U.S. Appl. No. 14/693,032, Notice of Allowance, dated Jun. 22, 2018.
U.S. Appl. No. 14/693,034, Nonfinal Office Action, dated May 17, 2017.
U.S. Appl. No. 14/693,034, Notice of Allowance, dated Oct. 25, 2017.
U.S. Appl. No. 14/693,039, Final Office Action, dated Dec. 15, 2017.
U.S. Appl. No. 14/693,039, Nonfinal Office Action, dated Jun. 5, 2017.
U.S. Appl. No. 14/693,039, Nonfinal Office Action, dated May 3, 2018.
U.S. Appl. No. 14/693,057, Final Office Action, dated Feb. 7, 2018.
U.S. Appl. No. 14/693,057, Nonfinal Office Action, dated Aug. 21, 2017.
U.S. Appl. No. 14/873,722, Final Office Action, dated Jun. 15, 2018.
U.S. Appl. No. 14/873,722, Nonfinal Office Action, dated Dec. 5, 2017.
U.S. Appl. No. 14/873,783, Final Office Action, dated May 23, 2018.
U.S. Appl. No. 14/873,783, Nonfinal Office Action, dated Dec. 8, 2017.
U.S. Appl. No. 14/873,823, Final Office Action, dated Jun. 29, 2018.
U.S. Appl. No. 14/873,823, Final Office Action, dated Mar. 15, 2017.
U.S. Appl. No. 14/873,823, Final Office Action, dated Nov. 3, 2017.
U.S. Appl. No. 14/873,823, Nonfinal Office Action, dated Feb. 23, 2018.
U.S. Appl. No. 14/873,823, Nonfinal Office Action, dated Jun. 21, 2017.
U.S. Appl. No. 14/873,823, Nonfinal Office Action, dated Nov. 30, 2016.
U.S. Appl. No. 14/873,864, Corrected Notice of Allowability, dated Jan. 18, 2018.
U.S. Appl. No. 14/873,864, Final Office Action, dated Dec. 2, 2016.
U.S. Appl. No. 14/873,864, Nonfinal Office Action, dated Apr. 5, 2017.
U.S. Appl. No. 14/873,864, Nonfinal Office Action, dated Jul. 14, 2016.
U.S. Appl. No. 14/873,864, Notice of Allowance, dated Aug. 28, 2017.
U.S. Appl. No. 14/873,864, Notice of Allowance, dated Dec. 21, 2017.
U.S. Appl. No. 14/873,914, Non final Office Action, dated Dec. 26, 2017.
U.S. Appl. No. 14/873,942, Non final Office Action, dated Nov. 22, 2017.
U.S. Appl. No. 14/873,942, Nonfinal Office Action, dated Mar. 16, 2018.
U.S. Appl. No. 15/409,248, filed Jan. 18, 2017, Konrardy et al., "Sensor Malfunction Detection".
U.S. Appl. No. 15/409,271, filed Jan. 18, 2017, Konrardy et al., "Autonomous Vehicle Component Malfunction Impact Assessment".
U.S. Appl. No. 15/409,305, filed Jan. 18, 2017, Konrardy et al., "Component Malfunction Impact Assessment".
U.S. Appl. No. 15/409,318, filed Jan. 18, 2017, Konrardy et al., "Automatic Repair of Autonomous Vehicles".
U.S. Appl. No. 15/409,336, filed Jan. 18, 2017, Konrardy et al., "Automatic Repair of Autonomous Components".
U.S. Appl. No. 15/409,340, filed Jan. 18, 2017, Konrardy et al., "Autonomous Vehicle Damage and Salvage Assessment".
U.S. Appl. No. 15/409,349, filed Jan. 18, 2017, Konrardy et al., "Component Damage and Salvage Assessment".
U.S. Appl. No. 15/409,359, filed Jan. 18, 2017, Konrardy et al., "Detecting and Responding to Autonomous Vehicle Collisions".
U.S. Appl. No. 15/409,371, filed Jan. 18, 2017, Konrardy et al., "Detecting and Responding to Autonomous Environment Incidents".
U.S. Appl. No. 15/409,445, filed Jan. 18, 2017, Konrardy et al., "Virtual Testing of Autonomous Vehicle Control System".
U.S. Appl. No. 15/409,473, filed Jan. 18, 2017, Konrardy et al., "Virtual Testing of Autonomous Environment Control System".
U.S. Appl. No. 15/859,859, filed Jan. 2, 2018, Hakmi-Boushehri et al., "Systems and Methods for Community-Based Cause of Loss Determination".
U.S. Appl. No. 15/895,149, filed Feb. 13, 2018, Jordan et al., Systems and Methods for Automatically Generating an Escape Route.
U.S. Appl. No. 17/077,785, Notice of Allowance, dated Jul. 14, 2022.
U.S. Appl. No. 14/692,864, Non final Office Action, dated May 16, 2017.
Yildirim et al., Fall detection using smartphone-based application, Int. J. Appl. Mathematics Electronics and Computers, 4(4):140-144 (2016).
Yu et al., A posture recognition-based fall detection system for monitoring an elderly person in a smart home environment, IEEE Tran. Infor. Tech. Biom., 16(6):1274-1286 (2012).

\* cited by examiner

SENSING PERIPHERAL HEURISTIC EVIDENCE, REINFORCEMENT, AND ENGAGEMENT SYSTEM

CROSS REFERENCE TO RELATED APPLICATIONS

This application is a continuation application of U.S. application Ser. No. 17/574,874, filed Jan. 13, 2022, entitled "SENSING PERIPHERAL HEURISTIC EVIDENCE, REINFORCEMENT, AND ENGAGEMENT SYSTEM," which is a continuation of U.S. application Ser. No. 17/077,785, filed Oct. 22, 2020, entitled "SENSING PERIPHERAL HEURISTIC EVIDENCE, REINFORCEMENT, AND ENGAGEMENT SYSTEM," which is a continuation of U.S. application Ser. No. 16/169,544, filed Oct. 24, 2018, which claims priority to and the benefit of: U.S. Application No. 62/654,975, filed Apr. 9, 2018, and entitled "SENSING PERIPHERAL HEURISTIC EVIDENCE, REINFORCEMENT, AND ENGAGEMENT SYSTEM," the entire disclosure of which is hereby incorporated herein in its entirety; and U.S. Application No. 62/658,682, filed Apr. 17, 2018, and entitled "SENSING PERIPHERAL HEURISTIC EVIDENCE, REINFORCEMENT, AND ENGAGEMENT SYSTEM," the entire disclosure of which is hereby incorporated herein in its entirety.

FIELD OF THE DISCLOSURE

The present disclosure generally relates to identifying a condition associated with an individual in a home environment.

BACKGROUND

As individuals age, many develop cognitive conditions or health conditions making it difficult and/or unsafe for them to live independently in a home environment. However, because the signs of such cognitive conditions and/or health conditions may be subtle, or may develop slowly over time, it may be difficult for caregivers to determine whether an individual is capable of safely living independently.

SUMMARY

In one aspect, a computer-implemented method for identifying a condition associated with an individual in a home environment may be provided. The method may include, via one or more local or remote processors, servers, transceivers, and/or sensors: (1) capturing data detected by a plurality of sensors associated with a home environment; (2) analyzing, by a processor, the captured data to identify one or more abnormalities or anomalies; and/or (3) determining, by a processor, based upon the identified one or more abnormalities or anomalies, a condition associated with an individual in the home environment. The method may additionally include (4) generating, by a processor, to a caregiver of the individual, a notification indicating the condition associated with the individual. The method may include additional, less, or alternate actions, including those discussed elsewhere herein.

In another aspect, a computer system for identifying a condition associated with an individual in a home environment may be provided. The computer system may include one or more sensors associated with a home environment, one or more processors configured to interface with the one or more sensors, and/or one or more memories storing non-transitory computer executable instructions. The non-transitory computer executable instructions, when executed by the one or more processors, cause the computer system to (1) capture data detected by the one or more sensors; (2) analyze the captured data to identify one or more abnormalities or anomalies; (3) determine, based upon the identified one or more abnormalities or anomalies, a condition associated with an individual in the home environment; and/or (4) generate, to a caregiver of the individual, a notification indicating the condition associated with the individual. The system may include additional, less, or alternate functionality, including that discussed elsewhere herein.

In still another aspect, a computer-readable storage medium having stored thereon a set of non-transitory instructions, executable by a processor, for identifying a condition associated with an individual in a home environment may be provided. The instructions include instructions for (1) obtaining data detected by a plurality of sensors associated with a home environment; (2) analyzing the captured data to identify one or more abnormalities or anomalies; (3) determining, based upon the identified one or more abnormalities or anomalies, a condition associated with an individual in the home environment; and/or (4) generating, to a caregiver of the individual, a notification indicating the condition associated with the individual. The instructions may direct additional, less, or alternate functionality, including that discussed elsewhere herein.

In still another aspect, a computer-implemented method for training a machine learning module to identify abnormalities or anomalies in sensor data corresponding to conditions associated with individuals in home environments may be provided. The computer-implemented method may include (1) receiving, by a processor, historical data detected by a plurality of sensors associated with a plurality of home environments; (2) receiving, by a processor, historical data indicating conditions associated with individuals in each of the plurality of home environments; (3) analyzing, by a processor, using a machine learning module, the historical data detected by the plurality of sensors associated with the plurality of home environments and the historical data indicating conditions associated with individuals in each of the plurality of home environments; and/or (4) identifying, by a processor, using the machine learning module, based upon the analysis, one or more abnormalities or anomalies in the historical data detected by the plurality of sensors corresponding to conditions associated with the individuals in the home environments. The method may include additional, less, or alternate actions, including those discussed elsewhere herein.

In still another aspect, a computer system for training a machine learning module to identify abnormalities or anomalies in sensor data corresponding to conditions associated with individuals in home environments may be provided. The computer system may include one or more processors and one or more memories storing non-transitory computer executable instructions. When executed by the one or more processors, the non-transitory computer executable instructions may cause the computer system to: (1) receive historical data detected by a plurality of sensors associated with a plurality of home environments; (2) receive historical data indicating conditions associated with individuals in each of the plurality of home environments; (3) analyze, using a machine learning module, the historical data detected by the plurality of sensors associated with the plurality of home environments and the historical data indicating conditions associated with individuals in each of the plurality of home environments; and/or (4) identify, using the machine learning module, based upon the analysis, one or more abnormalities or anomalies in the historical data detected by the plurality of sensors corresponding to conditions associated with the individuals in the home environments. The system may include additional, less, or alternate functionality, including that discussed elsewhere herein.

In still another aspect, a computer-readable storage medium having stored thereon a set of non-transitory instructions, executable by a processor, for training a machine learning module to identify abnormalities or anomalies in sensor data corresponding to conditions associated with individuals in home environments may be provided. The instructions may include instructions for: (1) receiving historical data detected by a plurality of sensors associated with a plurality of home environments; (2) receiving historical data indicating conditions associated with individuals in each of the plurality of home environments; (3) analyzing, using a machine learning module, the historical data detected by the plurality of sensors associated with the plurality of home environments and the historical data indicating conditions associated with individuals in each of the plurality of home environments; and/or (4) identifying, using the machine learning module, based upon the analysis one or more abnormalities or anomalies in the historical data detected by the plurality of sensors corresponding to conditions associated with the individuals in the home environments. The instructions may direct additional, less, or alternate functionality, including that discussed elsewhere herein.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the system and methods disclosed therein. It should be understood that each Figure depicts one embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein.

Figure 1:
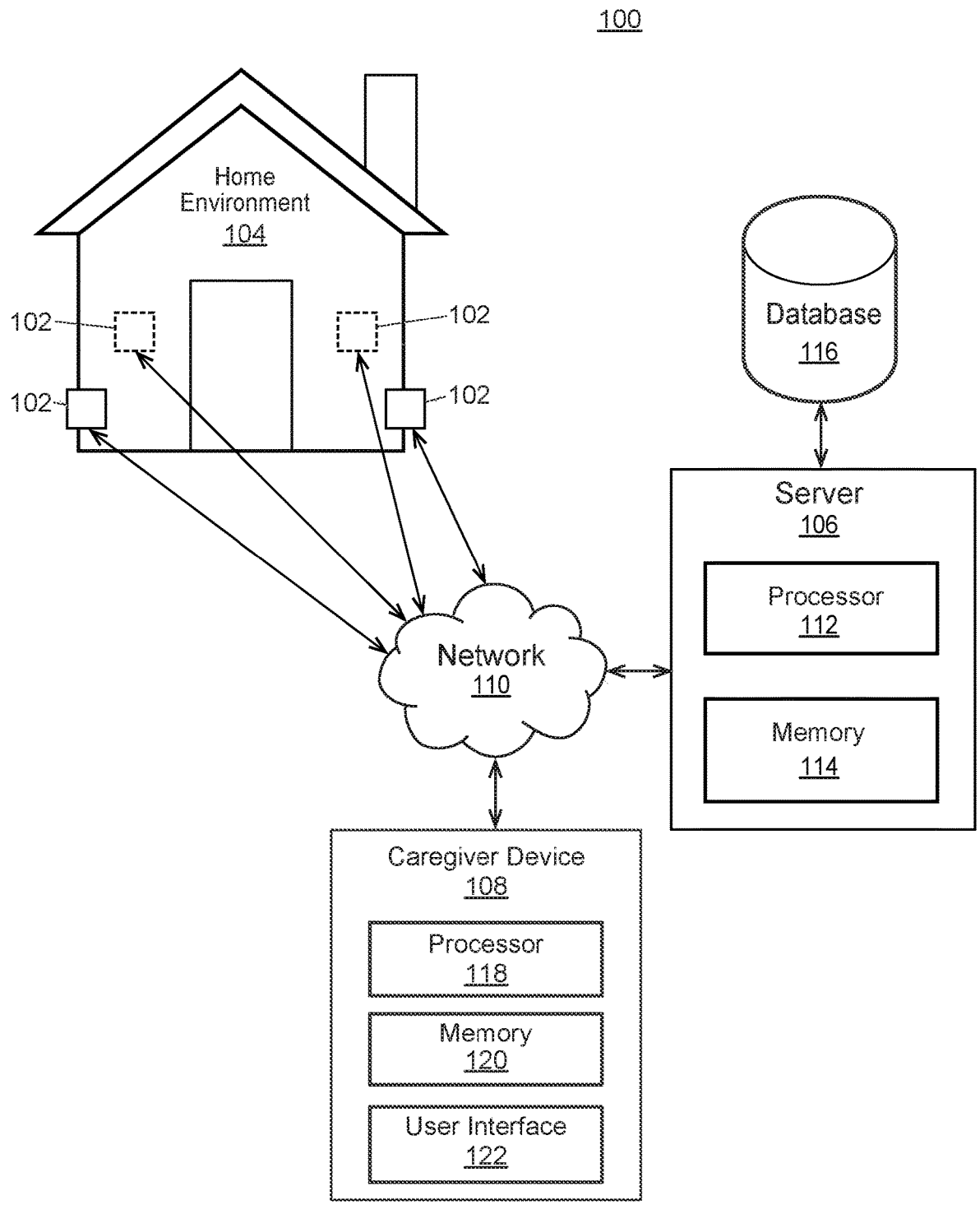
FIG. 1 illustrates an exemplary computer system for identifying a condition associated with an individual in a home environment, in accordance with some embodiments.

The Figures depict preferred embodiments for purposes of illustration only. One skilled in the art will readily recognize from the following discussion that alternative embodiments of the systems and methods illustrated herein may be employed without departing from the principles of the invention described herein.

DETAILED DESCRIPTION

As discussed above, individuals may develop cognitive conditions or health conditions making it difficult and/or unsafe for them to live independently in a home environment. However, because the signs of such cognitive conditions and/or health conditions may be subtle, or may develop slowly over time, it may be difficult for caregivers to determine whether an individual is capable of safely living independently.

Accordingly, systems and methods for identifying conditions associated with an individual in a home environment are provided herein. Sensors associated with the home environment may passively detect data, which may be captured and analyzed by a processor in order to identify potential conditions associated with an individual in the home environment. In some instances, the sensors may include sensors configured to capture data indicative of electricity use by devices associated with the home environment, including, e.g., which devices are using electricity, what date/time electricity is used by each device, how long each device uses electricity, and/or the power source for the electricity used by each device. The processor may analyze the captured data to identify any abnormalities or anomalies, and, based upon any identified abnormalities or anomalies, the processor may determine a condition (e.g., a medical condition, or a deviation from normal routines or activity) associated with an individual in the home environment. The processor may generate a notification indicating the condition associated with the individual to a caregiver of the individual. Advantageously, the caregiver may be informed of any conditions associated with the individual that may arise.

Moreover, in some embodiments, the systems and methods for identifying conditions associated with an individual in a home environment may include systems and methods for training a machine learning module to identify abnormalities or anomalies in sensor data corresponding to conditions associated with individuals in home environments. For instance, historical sensor data associated with home environments and corresponding historically identified conditions associated with individuals in the home environments may be used as inputs for a machine learning module to develop a predictive model identifying which a potential condition associated with an individual in a home environment using abnormalities or anomalies in the sensor data associated with the home environment.

The systems and methods provided herein therefore offer numerous benefits. In particular, the systems and methods effectively, efficiently, and non-intrusively, identify conditions associated with an individual in a home environment and provide a notification to a caregiver associated with the individual indicating any identified conditions, allowing a caregiver outside of the home environment to be informed of the status of the individual. In this way, the safety of the individual in the home environment may be improved. That is, because the caregiver will be alerted of conditions affecting the individual, which may include health conditions, cognitive conditions, etc., the caregiver may provide any assistance needed to the individual. Moreover, the caregiver outside the home environment may be able to use the information provided to continually assess whether the individual may continue to safely live independently in the home environment, and accordingly make changes in the individual's care when needed.

Furthermore, according to certain implementations, the systems and methods may support a dynamic, real-time or near-real-time analysis of any captured, received, and/or detected data. In particular, in some embodiments, a caregiver device may receive an indication of a condition associated with the individual in the home environment in real-time or near real-time, and may automatically and dynamically take actions such as requesting emergency medical assistance when needed. In this regard, any caregiver is afforded the benefit of accurate and relevant data, and may provide immediate care and assistance as needed.

Exemplary Computer System

Turning to FIG. 1, an exemplary computer system 100 for identifying a condition associated with an individual in a home environment is illustrated. The high-level architecture illustrated in FIG. 1 may include both hardware and software applications, as well as various data communications channels for communicating data between the various hardware and software components, as is described below.

The computer system 100 may include one or more sensors 102 associated with a home environment 104 such as, e.g., a house, apartment, condominium, or other living space associated with an individual. The computer system 100 further includes a server 106, and a caregiver device 108, each of which may communicate with one another (and/or with the sensors 102) using one or more network 110, which may be a wireless network, or which may include a combination of wireless and wired networks.

The sensors 102 may include, for example, electrical use sensors configured to detect data indicating, e.g., which outlets within the home environment are using electricity, which devices within the home environment are using electricity, the amount of electricity used by each device, dates and/or times at which each device uses electricity, the duration of time for which each device uses electricity, the power source for each device's electricity use (e.g., standard power sources versus generator in emergency situation), etc. Devices within the home environment may include appliances (e.g., stoves (including ignition sources for gas stoves), ovens, dishwashers, washers, dryers, refrigerators, freezers, microwaves, etc.), electronic devices (e.g., televisions, telephones, computers, etc.), heating and cooling devices (e.g., HVAC unit, furnace, hot water heater, etc.), lighting devices (e.g., overhead lights, lamps, etc.), water pumps, garage door openers, alarm systems, exercise equipment (e.g., treadmills, stationary bikes, elliptical machines, etc.), etc.

Additionally, in some instances, the sensors 102 associated with the home environment may also include smart sensors, or sensors associated with smart phones or other "smart" devices (i.e., devices connected to cellular and/or internet networks, or otherwise able to communicate with other devices, e.g., using Bluetooth) within the home environment, such as, e.g., virtual assistant devices, smart home devices, smart thermostats, smart appliances (e.g., smart ovens, smart dishwashers, smart washers, smart dryers, smart refrigerators, smart freezers, smart microwaves, etc.), smart lighting systems, smart speaker systems, smart robotics (e.g., smart robotic vacuums), smart motion sensors, smart water sensors, smart gas and ignition monitors, smart contact sensors, smart air movement and/or draft sensors, smart HVAC systems, smart pet monitor devices, smart medication dispensers, smart wearable electronics, smart alarm systems or security systems, smart scales, or any other suitable smart devices.

Moreover, in some instances, additional data may be captured by other suitable sensors 102 or other devices associated with the home environment (not shown), e.g., geo-locator tags associated with the home environment, weather monitoring devices associated with the home environment, vehicle sensors associated with the home environment (or with an individual within the home environment), wireless internet usage monitors, 3D printers, nanobots, fine motor control measurement devices, or any other suitable sensors or devices.

The sensors 102 may be configured to detect many different types of data, including but not limited to video data, image data, audio and/or decibel data, activity and/or movement data, vibration data, light data, arm/disarm data (i.e., with respect to an alarm system), body temperature data associated with the individual, home environment temperature data, moisture data, odor data, heart rate data associated with the individual, breathing rate data associated with the individual, hydration data associated with the individual, weight data associated with the individual, glucose/ketones levels associated with the individual, medication adherence data, travel and/or location data associated with the individual, socialization data associated with the individual, medical/health monitor device use data associated with the individual, appliance use data associated with the individual, electronics use data associated with the individual, air quality data, air quality data, sleep data associated with the individual, eye movement data associated with the individual, exercise data associated with the individual, body control data associated with the individual, fine motor control data associated with the individual, speech data associated with the individual, health and/or nutrition data associated with the individual, hygiene data associated with the individual, sight and/or hearing data associated with the individual, etc. Accordingly, this data may be communicated to the server 106 and/or caregiver device 108 via the network 110.

The server 106 may in some instances be a collection of multiple co-located or geographically distributed servers, etc. Additionally, although only one server 106 is shown in FIG. 1, there may be many servers 106. Furthermore, the server may include a processor 112 and a memory 114. The processor 112 may in some embodiments include multiple processors, and may be configured to execute any software applications residing on the memory 114. The software applications may be configured to analyze the data detected by the sensors 102 to determine information associated with individuals in the home environment 104.

For example, by analyzing the data detected by the sensors 102, the server 106 may determine indications of, e.g., presence (in particular locations or in the home environment generally), walking patterns, falls, hazards, imminent danger, evidence of atypical behavior (physical, mental, emotional, social), intruders in the home environment, theft in the home environment, fraud, abuse, position of furniture (e.g., for safety layout recommendations), trips, falls and other hazards, moisture and/or puddles on the floor or other surfaces or ceiling, whether lights are on or off, typical and atypical voice patterns (e.g., representing stoke, Alzheimer's detection, hearing decline, cognitive decline), socialization (such as decline in conversation or detecting other people in the house), falls, behavioral change (e.g., more aggression, more arguing, less conversation than usual) laughter, crying, other sounds relating to emotion, vehicle coming and going, movements of the individual from room to room, pace and speed of movement of the individual, duration of time spent in a space by the individual, time the individual spends outside of the house, atypical movements (e.g., seizures, movements before or after a fall or injury) walking patterns and/or gaits, movements and activities related to cooking, cleaning, exercise, entertainment, socialization, movements associated with a trip or stumble, eye movement, fall and impact level of fall, items dropping or breaking, entrance and or exit of the individual into or out of the home environment, tornados, earthquakes, other disaster events, phone calls and/or texts, vehicles coming and/or going, locations in the home environment where lights are turned on or off, for time duration of lights turned on and/or off, date of activation, activity of automatic lights that activate when movement or other stimulus is detected, alarm activation and/or disarm, alarm activation with no disarm, number of times over an amount of time, such as hour or single day an alarm is armed and disarmed, frequency or amount of accidental alarm activations, exit times when alarm is armed, home environment temperature (e.g., highs, lows, averages), hot water temperature from heater, faucets, and bathtub/showers, oven or stovetop temperatures, body temperature of inhabitants, differentiation of temperature between rooms of the house, opening and/or closing of vents, plumbing leaks, sump pump activation/issue, humidity averages and out of average range in the home environment, bed wetting or accidents, carbon monoxide, carbon dioxide, air quality, smoke, stagnant air, mold/mildew, ammonia, body odor, feces, pet, urine, natural gas, burning food, presence of certain foods, medical information associated with the individual (such as heart rate, blood pressure, cholesterol, glucose, ketones, weight, hydration, nutrition, medication adherence, medical device use or adherence, breathing rate), GPS location, travel itinerary, routine locations traveled to, mode of travel (e.g., plane, train, automobile, ride sharing services), travel services, duration of travel, travel delays, travel interruptions or difficulties, interaction routines, individuals with whom the individual frequently interacts, frequency of interactions, types of interactions, internet usage or activity, streaming television shows or movies, social media interaction or activity, social media postings, email usage, etc.

Moreover, the memory 114 may include multiple memories, which may be implemented as semiconductor memories, magnetically readable memories, optically readable memories, biologically readable memories, and/or any other suitable type(s) of non-transitory, computer-readable storage media. Additionally, the server may be configured to access a database 116 (e.g., via the network 110), which may store data related to, inter alia, behavioral patterns of individuals in the home environment 104, conditions associated with individuals in the home environment 104, or other suitable information associated with individuals in the home environment 104, etc. In some instances, blockchain encryption may be implemented to securely store this data. The data stored by the database 116 may be used by any software applications stored in the memory 114.

For example, various software applications stored in the memory 114 may be configured to analyze the information associated with the individual to identify abnormalities or anomalies associated with the individual (e.g., abnormalities or anomalies in the individual's behaviors). Based upon the identified abnormalities or anomalies, a condition associated with an individual in the home environment may be determined. Specifically, the condition (e.g., a medical condition, cognitive condition, etc.) may be determined based upon atypical behaviors of the individual indicated by the identified abnormalities or anomalies. Based upon the condition, the software applications may be configured to generate a notification for a caregiver of the individual, and/or transmit the notification to a caregiver device 108.

The caregiver device 108 may be, for instance, a personal computer, cellular phone, smart phone, tablet computer, smart watch, a wearable electronic device such as a fitness tracker, a dedicated caregiver device, or any other suitable mobile device associated with a caregiver of an individual in the home environment 104. Furthermore, the caregiver device 108 may include a processor 118 and a memory 120. The processor 118 may in some embodiments include multiple processors, and may be configured to execute any software applications residing on the memory 120. Moreover, the memory 120 may include multiple memories, which may be implemented as semiconductor memories, magnetically readable memories, optically readable memories, biologically readable memories, and/or any other suitable type(s) of non-transitory, computer-readable storage media. Additionally, the caregiver device 108 may include a user interface 122 (e.g., a display configured to display a user interface), upon which notifications, alerts, etc. may be displayed, as discussed in greater detail with respect to FIG. 3 below.

Exemplary Home Environment

Figure 2:
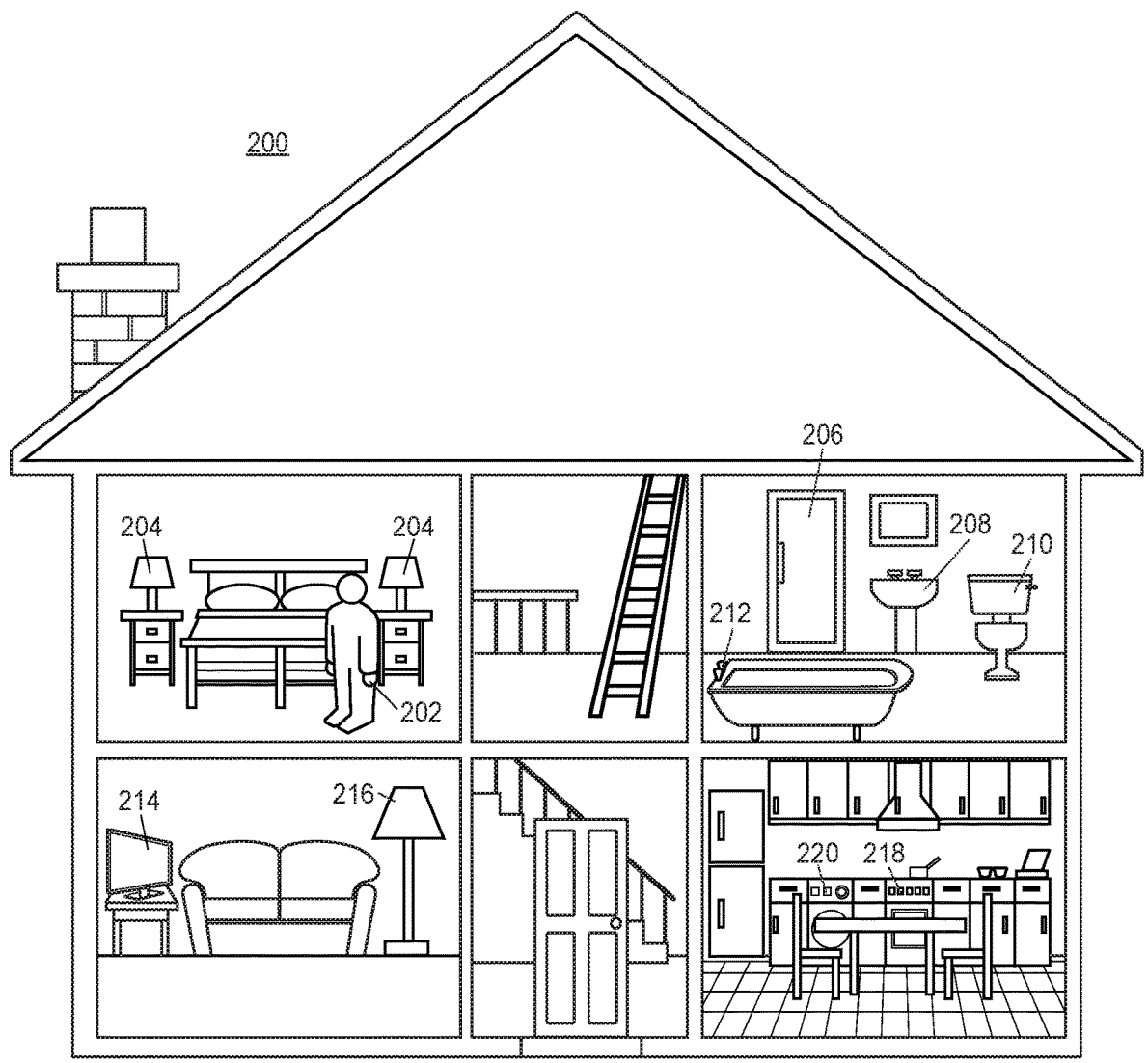
FIG. 2 illustrates an exemplary home environment, in accordance with some embodiments.

Turning now to FIG. 2, an exemplary home environment 200 is illustrated, in accordance with some embodiments. An individual 202 in the home environment 200 may use devices within the home environment 200 as part of a daily routine. For example, the individual 202 may wake up every morning and switch on a lamp 204 before using a shower 206 (and/or sink 208, toilet 210, or bath 212). Next, the individual 202 may switch on a television 214, check emails or social media posting, and/or a living room lamp 216, before making breakfast using a stove 218 or oven 220.

Data captured by electrical use sensors (or other sensors in the home environment) 102 indicating the typical usage of each of these devices within the home environment 200 may be utilized to establish patterns and/or routines associated with the individual 202. For example, data captured by electrical use sensors indicating that the lamp 204 uses electricity starting every morning at 6:00 a.m. may indicate that the individual 202 has a pattern or routine of waking every morning at 6:00 a.m. As another example, data captured by electrical use sensors indicating that the television 214 uses energy for 2-3 hours per day may indicate that the individual 202 has a pattern or routine of watching 2-3 hours of television per day.

Of course, other of the sensors 102 may also be utilized to establish patterns and/or routines associated with the individual 202 in various embodiments. For instance, data stored by smart lighting may indicate usage times of various lamps within the home environment, data stored by a smart television may indicate the duration of use of the television, data stored by a laptop or other computer may indicate usage times of the internet or streaming television shows, internet usage may also indicate social media usage or time-of-day usage, etc.

By analyzing the captured data, information about the behaviors of the individual within the home environment may be determined. Specifically, the captured data may be analyzed to identify abnormalities or anomalies. Based upon the identified abnormalities or anomalies, a condition associated with an individual in the home environment may be determined. Specifically, the condition (in some instances, a medical condition) may be determined based upon atypical behaviors of the individual indicated by the identified abnormalities, abnormalities, or shifts in behavior patterns. Consequently, a notification indicating the condition associated with the individual 202 may be generated and/or displayed for a caregiver of the individual (such as a parent, child, spouse, doctor, nurse, or other medical caregiver, assisted living facility caregiver or other professional caregiver, etc.), e.g., via a caregiver device 108.

Exemplary User Interface

Figure 3:
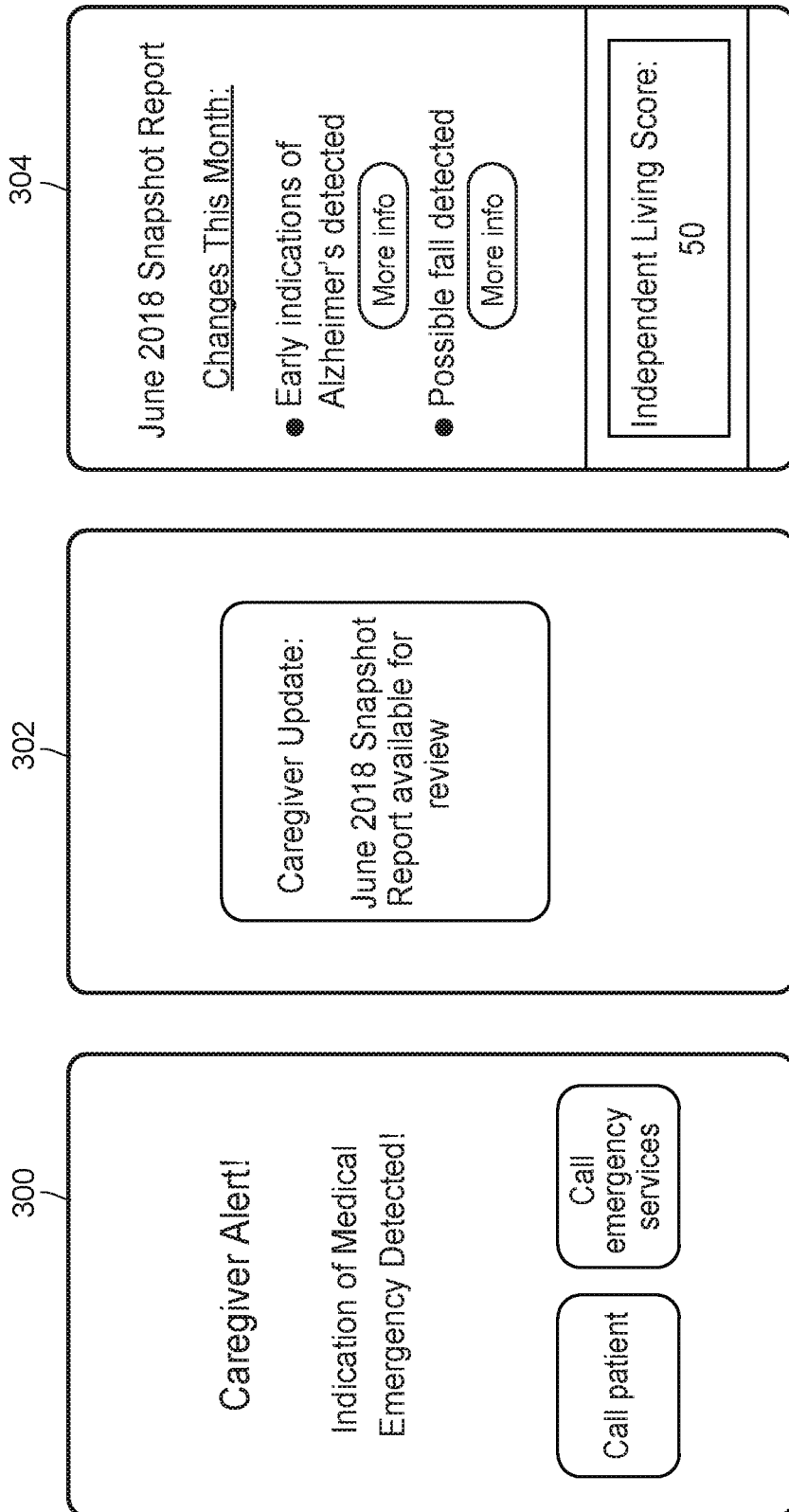
FIG. 3 illustrates several exemplary user interface displays, in accordance with some embodiments.

FIG. 3 illustrates several exemplary user interface displays 300, 302, 304 generated and displayed for a caregiver (e.g., via a caregiver device 108) of an individual in a home environment based upon the data captured by the sensors 102. For example, user interface display 300 displays an alert indicating that a medical emergency associated with the individual in the home environment has been detected. Consequently, the caregiver may be presented with options to call the individual, and/or to call an emergency service (e.g., medical services, fire services, police services, etc.)

As another example, user interface display 302 displays an update indicating that a snapshot report for June 2018 is available for caregiver review. User interface display 304 displays an exemplary June 2018 Snapshot report associated with the individual in the home environment, generated for the caregiver of the individual.

In various embodiments, snapshot reports as shown in user interface display 304 may be generated periodically (e.g., daily, weekly, and/or yearly), showing the individual's progress or decline in various areas, as well as items of potential concern. In some instances, the snapshot report may further include an indication of, e.g., whether the individual is able to live independently, whether the individual may need assistance, whether a fall or injury may have occurred, whether the individual is bathing, eating, or sleeping, potential cognitive or medical issues, whether the individual is taking his or her medication and/or whether the medication is helping the individual, etc. For example, as shown in exemplary user interface display 304, the snapshot report includes a notification that early signs of Alzheimer's disease have been detected in the individual, and that a possible fall has been detected.

In various embodiments the report may include one or more of customized time period reports, comparative timeframe reports, an indication of the number of notifications sent to caregiver and for what, medication taken, for what, and if that medication is working, areas of concern, areas of decline, areas where intervention or improvement needs to take place, areas where the individual needs assistance or additional assistance, suggested and/or recommend actions to be taken by an individual or by a caregiver, recommended services, support, and resources within a certain proximity of the location, number ranges of optimal (based upon age/ability) levels of physical, mental, social, and emotional engagement, activity, and/or ability, goals and/or goal setting/meeting features, etc. In some instances, the report may include an independent living overall score (e.g., with 100 representing ideal independent living capability, 70 representing family/support services interaction needed for independent living capability, 60 representing significant family/support services interaction needed to live independently, 50 and below representing professional assistance needed, etc.). For example, as shown in exemplary user interface display 304, the snapshot report includes an independent living score of 50.

Figure 4:
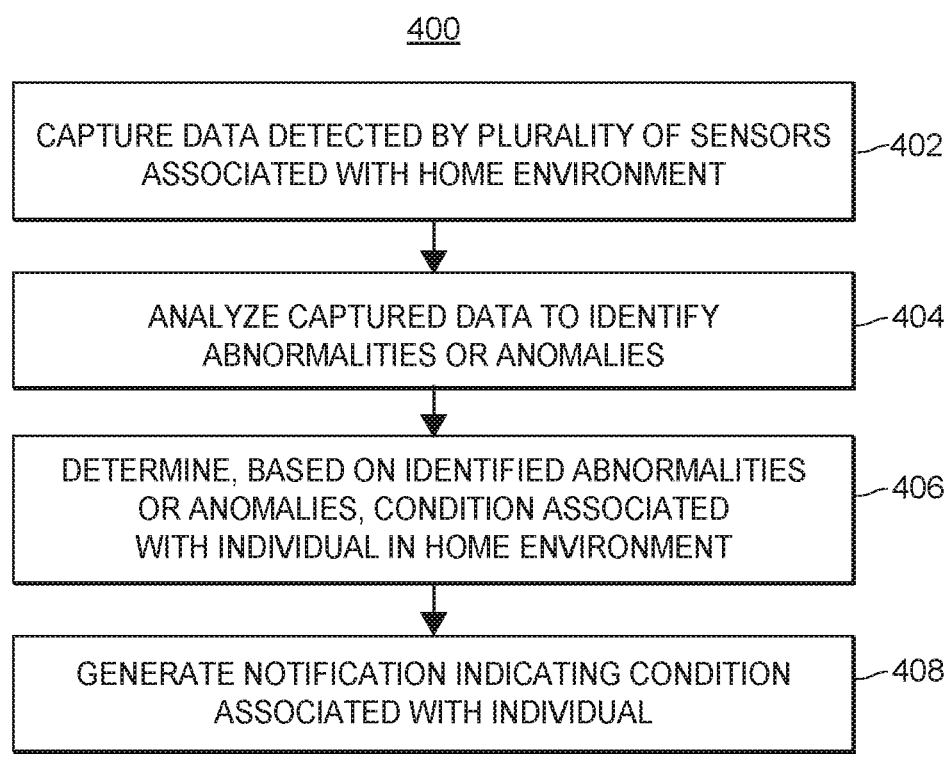
FIG. 4 illustrates a flow diagram of an exemplary computer-implemented method for identifying a condition associated with an individual in a home environment, in accordance with some embodiments.

Exemplary Computer-Implemented Method for Identifying Condition Associated with Individual in Home Environment Turning now to FIG. 4, a flow diagram of an exemplary computer-implemented method 400 for identifying a condition associated with an individual in a home environment is illustrated, in accordance with some embodiments. The method 400 can be implemented as a set of instructions stored on a computer-readable memory and executable on one or more processors.

At block 402, data detected by a plurality of sensors (e.g., sensors 102) associated with a home environment (e.g., home environment 104) is captured. For example, an electrical use sensor may detect that, at a given time, an oven in the home environment is currently using electricity. As another example, an electrical use sensor may detect data indicating that a lamp in the home environment uses power on weekdays starting at 6:00 a.m., and on weekends starting at 8:00 a.m. As still another example, an electrical use sensor may detect data indicating that a water pump in the home environment has been operating for a certain amount of time (e.g., 15 minutes, one hour, all day, etc.). As an additional example, an electrical use sensor may detect that a furnace in the home environment is using power from a power generator.

By analyzing the captured data, information about the behaviors of the individual within the home environment may be determined. In some instances, the information indicated by the captured data may relate to current behaviors of the individual. For example, data from an electrical use sensor indicating that an oven in the home environment is currently using electricity may indicate that an individual in the home environment is currently cooking a meal. As another example, from an electrical use sensor indicating that a water pump in the home environment has been operating for a certain amount of time (e.g., 15 minutes, one hour, all day, etc.) may indicate that an individual within the home environment is currently taking a shower or a bath.

Additionally, over time, the information indicated by the captured data may be used to determine patterns in the behaviors of the individual. In other words, the captured data may be analyzed to identify data patterns indicative of behavior patterns. For instance, data from an electrical use sensor indicating that a lamp in the home environment uses power every day starting at 6:00 a.m. may indicate that an individual within the home environment wakes up around 6:00 a.m. each morning. Similarly, data from an electrical use sensor indicating that a water pump in the home environment typically operates for 15 minutes at 6:30 a.m. may indicate that the individual typically showers at 6:30 a.m. each morning.

At block 404, the captured data is analyzed to identify abnormalities or anomalies. The captured data may be compared against identified patterns in order to identify instances in which the data is inconsistent with the identified patterns, which may in turn indicate abnormalities or anomalies in the behaviors of the individual. For instance, in the example described above, an identified pattern in the electrical usage of a lamp in the home environment starting at 6:00 a.m. may indicate a typical wake-up time of 6:00 a.m. for an individual in the home environment. However, if the captured data indicates that one day the lamp does not use electricity until 8:00 a.m., an anomaly or abnormality may be identified for that day. This captured data may in turn indicate an anomaly or abnormality in the behavior of the individual, i.e., that the individual woke up later than usual on that day.

As another example, data from an electrical use sensor may indicate that a water pump in the home environment operates once per day for 15 minutes, which may in turn indicate that the user showers every day. However, if the captured data indicates that one day the water pump does not operate, or operates for a time duration shorter than a typical shower (e.g., only operates for 2 minutes), an abnormality or anomaly may be identified for that day. This captured data may in turn indicate an abnormality or anomaly in the behavior of the individual, i.e., that the individual did not shower on that day.

In some instances, analyzing the captured data to identify abnormalities or anomalies may include analyzing the captured data to identify the emergence of new behavior patterns, or shifts in behavior patterns of the individual. For instance, using the example described above, over several years, an identified pattern in the electrical usage of a lamp (or television or computer) in the home environment starting at 6:00 a.m. may indicate a typical wake-up time of 6:00 a.m. for an individual in the home environment over those several years. However, over the most recent month, a new pattern in the electrical usage of the lamp may emerge, indicating a new typical wake-up time of 8:00 a.m. for the individual in the home environment.

As another example, a pattern in the electrical usage of a stove or oven may indicate that an individual in the home environment uses the stove or oven (likely to cook a meal) five times per week over the course of six months. However, over the most recent six months, a new pattern in the electrical usage of the stove or oven may emerge, indicating that the individual in the home environment uses the stove or oven (likely to cook a meal) only one time per week.

At block 406, a condition associated with an individual in the home environment is determined based upon the identified abnormalities or anomalies. Specifically, the condition (in some instances, a medical condition) may be determined based upon atypical behaviors of the individual indicated by the identified abnormalities, abnormalities, or shifts in behavior patterns. For example, if the captured data indicates that a user has left a stove or oven on for an atypically long time, a forgetfulness condition associated with the individual may be determined (i.e., because the user likely forgot that the stove or oven was on).

As another example, if the captured data previously indicated that the individual likely showered once per day, and the capture data indicates that the individual currently showers only once per week, a hygiene condition associated with the individual may be determined (i.e., because the individual is likely bathing less frequently). As still another example, if the captured data indicates that the individual wakes up at a time that is atypically late, an insomnia or fatigue condition associated with the individual may be determined.

Other atypical behaviors that may be detected based upon identified abnormalities or anomalies may include, for instance, lights not being turned on/off, changes in laundry habits, refrigerator not opening and closing, alarm not armed or disarmed, slurred speech when using a voice assistant or passive listening, change in gait, water running too long (i.e., suggesting a shower fall or cognitive failure), sensing a large mass has quickly flattened (i.e., suggesting a fall has occurred).

At block 408, a notification indicating the condition associated with the individual is generated. The notification may be displayed to a caregiver of the individual, such as a parent, child, spouse, doctor, nurse, or other medical caregiver, assisted living facility caregiver or other professional caregiver, etc. In some instances, the notification may indicate a specific event, such as a fall, an entrance or an exit, a travel event, a medical event, or another critical event associated with the individual.

In some examples, when the condition associated with the individual is an emergency medical condition or other urgent condition, a request for emergency services to be provided to the individual may be generated. For instance, ambulance, police, or fire services may be requested.

In some instances, e.g., as shown in FIG. 3, the notification may be a digital "snapshot" report generated periodically (e.g., daily, weekly, and/or yearly), showing the individual's progress or decline in various areas, as well as items of potential concern. The report may further include an indication of, e.g., whether the individual is able to live independently, whether the individual may need assistance, whether a fall or injury may have occurred, whether the individual is bathing, eating, or sleeping, potential cognitive issues, whether the individual is taking his or her medication and/or whether the medication is helping the individual, etc. In some instances, the reports may be configured to be shared with medical professionals, family members, caregivers, etc. Blockchain encryption may be implemented in some instances to keep the report information secure.

Exemplary Computer-Implemented Method for Training Machine Learning Module

Figure 5:
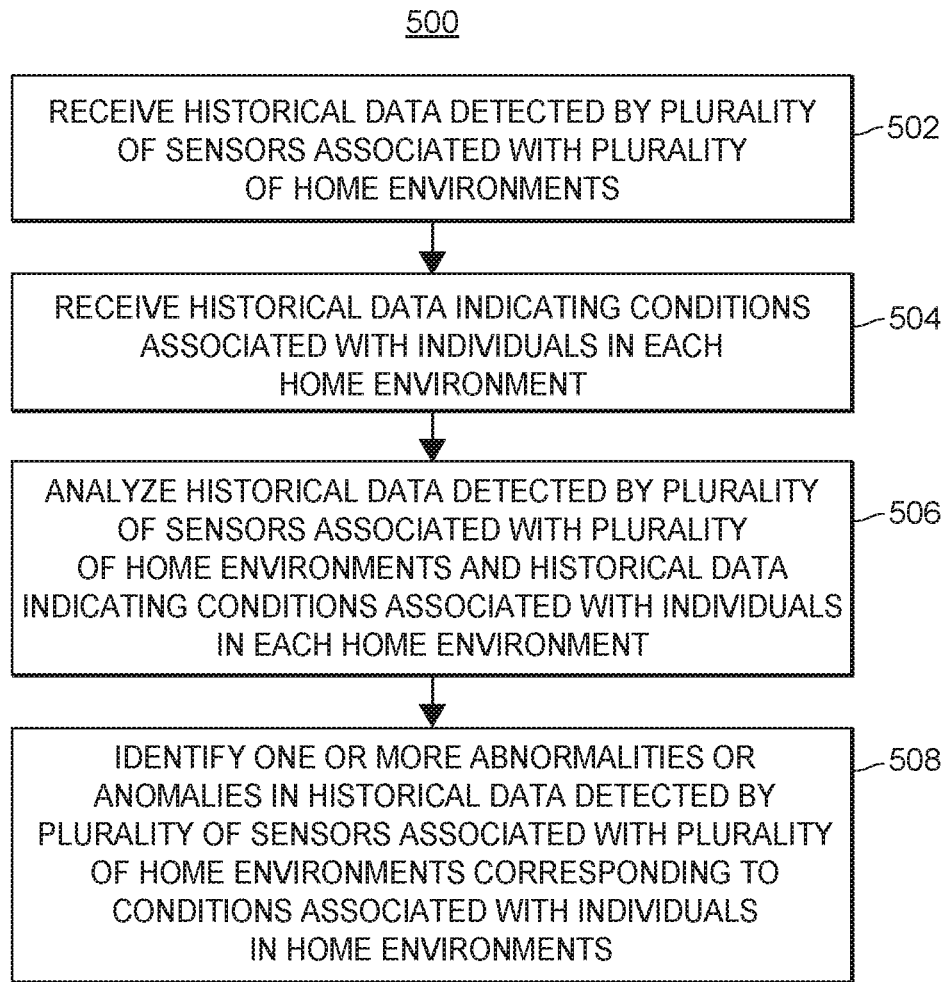
FIG. 5 illustrates a flow diagram of an exemplary computer-implemented method for training a machine learning module to identify abnormalities or anomalies in sensor data corresponding to conditions associated with individuals in home environments, in accordance with some embodiments.

Turning now to FIG. 5, a flow diagram of an exemplary computer-implemented method 500 for training a machine learning module to identify abnormalities or anomalies in sensor data corresponding to conditions associated with individuals in home environments is illustrated, in accordance with some embodiments. The method 500 can be implemented as a set of instructions stored on a computer-readable memory and executable on one or more processors.

At block 502, historical data detected by a plurality of sensors (e.g., sensors 102) associated with a plurality of home environments (e.g., home environment 104) may be received. In some instances, the historical sensor data may be received upon accessing a database (e.g., database 116). Similarly, at block 504, historical data indicating one or more conditions associated with the individuals in each home environment may be received. In some instances, the historical data may be received upon accessing a database (e.g., database 116).

At block 506, the historical data detected by the plurality of sensors associated with the plurality of home environments and the historical data indicating conditions associated with individuals in each home environment may be analyzed using a machine learning module (or artificial intelligence, or other machine learning models, programs, or algorithms). That is, the historical sensor data and/or the historical condition data may be used as input for the machine learning module, which may employ a neural network, which may be a convolutional neural network, a deep learning neural network, or a combined learning module or program that learns in two or more fields or areas of interest. Re-inforced or reinforcement learning techniques may also be used.

The machine learning module's analysis of the historical sensor data and the historical condition data may include identifying and recognizing patterns in the data, including the types of data and usage data discussed herein. In some embodiments, existing data, including usage, text or voice/speech data may be used in order to facilitate making predictions for subsequent data. Voice recognition and/or word recognition techniques may also be used. Models may be created based upon example inputs in order to make valid and reliable predictions for novel inputs.

Additionally or alternatively, the machine learning programs may be trained by inputting sample data sets or certain data into the programs, such as mobile device, smart home, smart home sensor, drone, autonomous or semi-autonomous drone, image, vehicle telematics, smart or autonomous vehicle, and/or intelligent home telematics data. In general, training the neural network model may include establishing a network architecture, or topology, and adding layers that may be associated with one or more activation functions (e.g., a rectified linear unit, softmax, etc.), loss functions and/or optimization functions. Data sets used to train the artificial neural network(s) may be divided into training, validation, and testing subsets; these subsets may be encoded in an N-dimensional tensor, array, matrix, or other suitable data structures.

Training may be performed by iteratively training the network using labeled training samples. Training of the artificial neural network may produce byproduct weights, or parameters which may be initialized to random values. The weights may be modified as the network is iteratively trained, by using one of several gradient descent algorithms, to reduce loss and to cause the values output by the network to converge to expected, or "learned", values. In an embodiment, a regression neural network may be selected which lacks an activation function, wherein input data may be normalized by mean centering, to determine loss and quantify the accuracy of outputs. Such normalization may use a mean squared error loss function and mean absolute error. The artificial neural network model may be validated and cross-validated using standard techniques such as hold-out, K-fold, etc. In some embodiments, multiple artificial neural networks may be separately trained and operated, and/or separately trained and operated in conjunction.

Furthermore, the machine learning programs may utilize deep learning algorithms that may be primarily focused on pattern recognition, and may be trained after processing multiple examples. The machine learning programs may include Bayesian program learning (BPL), voice recognition and synthesis, image or object recognition, optical character recognition, and/or natural language processing—either individually or in combination. The machine learning programs may also include natural language processing, semantic analysis, automatic reasoning, and/or other machine learning techniques, including those discussed elsewhere herein.

In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. In unsupervised machine learning, the processing element may be required to find its own structure in unlabeled example inputs.

At block 508, one or more abnormalities or anomalies in the historical data detected by the plurality of sensors corresponding to the conditions associated with the individuals in the home environments may be identified using a machine learning module, based upon the analysis. The identified abnormalities or anomalies in the historical data and their corresponding conditions may comprise a predictive model to be used to analyze current sensor data. For example, the model may include a prediction of a condition associated with an individual in the home environment based upon certain abnormal or anomalous patterns in current sensor data.

In some instances, certain aspects of the exemplary computer-implemented method 500 may be combined with aspects of the exemplary computer-implemented method 400. For example, the identified abnormalities or anomalies in the historical data and their corresponding conditions discussed with respect to block 508 may be utilized in the analysis discussed with respect to block 404 of the method 400, e.g., by comparing the one or more abnormalities or anomalies in current sensor data to the identified abnormalities or anomalies in the historical data and their corresponding conditions. Of course, additional or alternative combinations of these methods may be envisioned in various embodiments.

Exemplary Systems & Methods for Anomaly Detection

In one aspect, a computer-implemented method for identifying a condition associated with an individual in a home environment may be provided. The method may include (1) capturing or receiving data detected by a plurality of sensors associated with a home environment, such as at one or more transceivers associated with one or more local or remote processors via wireless transmission or data transmission over one or more radio frequency links; (2) analyzing, by the one or more local or remote processors, the captured or received sensor data to identify one or more abnormalities or anomalies; (3) determining, by the one or more local or remote processors, based upon the identified one or more abnormalities or anomalies, a condition associated with an individual in the home environment; (4) generating, by the one or more local or remote processors a notification indicating the condition associated with the individual; and/or (5) transmitting, by the one or more local or remote processors and/or associated transceivers the notification to a caregiver mobile device, the caregiver being associated with the individual. The method may include additional, less, or alternate actions, including those discussed elsewhere herein.

In another aspect, a computer system for identifying a condition associated with an individual in a home environment may be provided. The system may include one or more sensors associated with a home environment; one or more local or remote processors and/or associated transceivers configured to interface with the one or more sensors; and one or more memories storing non-transitory computer executable instructions that, when executed by the one or more processors, cause the computer system to: (1) capture data detected by the one or more sensors, or receive data generated by the one or more sensors, such as data wirelessly communicated over one or more radio frequency links; (2) analyze the captured data to identify one or more abnormalities or anomalies; (3) determine, based upon the identified one or more abnormalities or anomalies, a condition associated with an individual in the home environment; (4) generate an electronic notification indicating the condition associated with the individual; and/or (5) transmit the electronic notification, such as via wireless communication or data transmission over one or more radio frequency links to a mobile device or other computing device associated with a caregiver associated with the individual. The system may include additional, less, or alternate functionality, including that discussed elsewhere herein.

In another aspect, a computer-implemented method for training a machine learning module to identify abnormalities or anomalies in sensor data corresponding to conditions associated with individuals in home environments may be provided. The method may include (1) receiving, by one or more local or remote processors, historical data detected by a plurality of sensors associated with a plurality of home environments; (2) receiving, by the one or more local or remote processors, historical data indicating conditions associated with individuals in each of the plurality of home environments; (3) analyzing, by the one or more local or remote processors, using a machine learning module, (i) the historical data detected by the plurality of sensors associated with the plurality of home environments, and/or (ii) the historical data indicating conditions associated with individuals in each of the plurality of home environments; and/or (4) identifying, by the one or more local or remote processors, using the machine learning module, based upon the analysis, one or more abnormalities or anomalies in the historical data detected by the plurality of sensors corresponding to conditions associated with the individuals in the home environments. The method may also include (5) capturing or receiving current data detected by a plurality of sensors associated with a home environment; (6) analyzing, by the one or more local or remote processors and/or the trained machine learning module, the captured current data to identify one or more abnormalities or anomalies in the current data; (7) comparing, by the one or more local or remote processors and/or the trained machine learning module, the one or more abnormalities or anomalies in the current data to the abnormalities or anomalies in the historical data detected by the plurality of sensors corresponding to conditions associated with the individuals in the home environments; and/or (8) determining, by the one or more local or remote processors and/or the trained machine learning module, based upon the comparison, a current condition associated with an individual in the home environment. The method may include additional, less, or alternate actions, including those discussed elsewhere herein.

In one aspect, a computer system for training a machine learning module to identify abnormalities or anomalies in sensor data corresponding to conditions associated with individuals in home environments may be provided. The system may include one or more local or remote processors and/or associated transceivers; and one or more memories storing non-transitory computer executable instructions that, when executed by the one or more processors and/or associated transceivers, cause the computer system to: (1) receive historical data detected by a plurality of sensors associated with a plurality of home environments; (2) receive historical data indicating conditions associated with individuals in each of the plurality of home environments; (3) analyze, using a machine learning module, (i) the historical data detected by the plurality of sensors associated with the plurality of home environments and/or (ii) the historical data indicating conditions associated with individuals in each of the plurality of home environments; and/or (4) identify, using the machine learning module, based upon the analysis, one or more abnormalities or anomalies in the historical data detected by the plurality of sensors corresponding to conditions associated with the individuals in the home environments. The system may include additional, less, or alternate functionality, including that discussed elsewhere herein.

In one aspect, a computer-implemented method for training a machine learning module to identify abnormalities or anomalies in sensor data corresponding to conditions associated with individuals in home environments may be provided. The method may include (1) receiving, by one or more local or remote processors and/or associated transceivers (such as via wireless communication or data transmission over one or more radio frequency links or communication channels), historical data detected by a plurality of sensors associated with a plurality of home environments; (2) receiving, by the one or more local or remote processors and/or associated transceivers, historical data indicating conditions associated with individuals in each of the plurality of home environments; (3) inputting, by the one or more local or remote processors, into a machine learning module (i) the historical data detected by the plurality of sensors associated with the plurality of home environments and/or (ii) the historical data indicating conditions associated with individuals in each of the plurality of home environments to train the machine learning module to identify one or more abnormalities or anomalies in the historical data detected by the plurality of sensors corresponding to conditions associated with the individuals in the home environments; (4) capturing current data detected by a plurality of sensors associated with a home environment, or receiving current data detected by the plurality of sensors associated with the home environment, via the one or more local or remote processors and/or associated transceivers; (5) inputting, by the one or more local or remote processors, the current data into the trained machine learning module to identify one or more abnormalities or anomalies in the current data and/or an individual in the current data; (6) generating, by the one or more local or remote processors, a notification regarding the one or more abnormalities or anomalies and/or the individual; and/or (7) transmitting, by the one or more local or remote processors and/or transceivers, the notification to a mobile or other computing device of a caregiver for the individual. The method may include additional, less, or alternate actions, including those discussed elsewhere herein.

In another aspect, a computer system configured to train a machine learning module to identify abnormalities or anomalies in sensor data corresponding to conditions associated with individuals in home environments may be provided. The system may include one or more local or remote processors, memories, sensors, transceivers, and/or servers configured to: (1) receive, such as via wireless communication or data transmission over one or more radio frequency links or communication channels, historical data detected by a plurality of sensors associated with a plurality of home environments; (2) receive, such as via wireless communication or data transmission over one or more radio frequency links or communication channels, historical data indicating conditions associated with individuals in each of the plurality of home environments; (3) input, into a machine learning module, (i) the historical data detected by the plurality of sensors associated with the plurality of home environments and/or (ii) the historical data indicating conditions associated with individuals in each of the plurality of home environments to train the machine learning module to identify one or more abnormalities or anomalies (and/or conditions associated with an individual) in the historical data detected by the plurality of sensors corresponding to conditions associated with the individuals in the home environments; (4) capture current data detected by a plurality of sensors associated with a home environment, or receive, such as via wireless communication or data transmission over one or more radio frequency links or communication channels, current data detected by the plurality of sensors associated with the home environment; (5) input the current data into the trained machine learning module to identify one or more abnormalities or anomalies in the current data and/or an individual in the current data; (6) generate an electronic notification regarding the one or more abnormalities or anomalies and/or the individual; and/or (7) transmit the electronic notification, such as via wireless communication or data transmission over one or more radio frequency links or communication channels, to a mobile or other computing device of a caregiver for the individual. The system may include additional, less, or alternate functionality, including that discussed elsewhere herein.

Other Matters

The computer-implemented methods discussed herein may include additional, less, or alternate actions, including those discussed elsewhere herein. The methods may be implemented via one or more local or remote processors, transceivers, servers, and/or sensors (such as processors, transceivers, servers, and/or sensors mounted on homes, mobile devices, vehicles, computers, televisions, drones, or associated with smart infrastructure or remote servers), and/or via computer-executable instructions stored on non-transitory computer-readable media or medium.

Additionally, the computer systems discussed herein may include additional, less, or alternate functionality, including that discussed elsewhere herein. The computer systems discussed herein may include or be implemented via computer-executable instructions stored on non-transitory computer-readable media or medium.

In some embodiments, a processor or a processing element may be trained using supervised or unsupervised machine learning, and the machine learning program may employ a neural network, which may be a convolutional neural network, a deep learning neural network, or a combined learning module or program that learns in two or more fields or areas of interest.

Exemplary Spheres Embodiments

In one embodiment, a SPHERES system may be provided. SPHERES— or Sensing Peripheral Heuristic Evidence, Reinforcement, and Engagement System—may be a network of passive smart systems (i.e., Electric use monitoring sensors, connected home assistant, connected smart home systems, connected video security and more) combined with AI/software to form a solution which autonomously and passively monitors and measures spheres of information, behaviors, and data points, looking for routines and changes to those routines. In one embodiment, the sensor or other data collected may provide actionable insights to caregivers based upon discrete data points, and may monitor routines of certain individuals at risk of medical or other issues.

From passive data collection, SPHERES enables live tracking and notification of the routine norms and abnormalities/anomalies, impacts and dangers within the data and provides instant digital notification when the system senses a change which could cause harm, injury, or loss, is an emergency, or needs immediate additional human interaction and follow-up.

The system also produces on-demand, daily, monthly, yearly, and custom time period-over-time period digital snapshots of collected data to easily understand changes (and red flags) in norms, routines, and behaviors. SPHERES reports include recommendations based upon the collected data points to improve user experience and engagement, increase safety or efficiency, decrease time to intervention/action, save money, or otherwise decrease negative aspects or improve positive impacts. To keep all this personal data safe, it is stored using Blockchain encryption.

One exemplary embodiment may be related to independent/senior living. Here, SPHERES, using electric monitoring sensors, connected smart home devices and assistants (such as Nest, Google Home, Amazon Alexa), and security devices (such as Canary and ADT), and a PERS device (such as Life Alert), a family caregiver could understand the daily routine of a semi-independent loved one, know instantly or within a short period of time, if there are red flags or emergencies which need interaction, and over time, have information they need to help the care recipient make informed independent living or enhanced caregiving environment choices.

In this example, SPHERES would monitor energy use within the home, such as when lights are turned on or off, when computers are activated, when water pumps are running, and when large appliances or TVs and devices are running, when a smart light activates or senses presence, and/or when a garage or other door open. SPHERES may also monitor security features such as cameras and alarm systems, and/or monitor home assistants, such as a voice-activated assistant.

SPHERES, using passive monitoring, keeps track of an independent living consumer's daily routine. Because humans are creatures of habit, trends/routines—such as sleep and wake time, breakfast, lunch, and dinner routines, entertainment themes, enter/exit themes, movement around house or property patterns, personal hygiene themes, etc.— may be formed. Additionally, everyone has their own walking pattern, speech pattern, and other patterns which are unique.

By using a connected network of smart appliances, devices, and systems, sensor technology, and AI/software data sorting and analysis, SPHERES can understand when something is typical or atypical, such as: lights not being turned on/off; changes in laundry habits; refrigerator not opening and closing; alarm not armed or disarmed; when speech is slurred when using a voice assistant or passive listening; a camera could sense a person's gate has changed maybe due to injury; water running too long could suggest a shower fall or cognitive failure; sensing a large mass similar to that of the resident has quickly flattened suggesting a fall has occurred; and/or many other data points and abnormalities in routine (including those mentioned elsewhere herein) suggesting action and caregiver instant notification is needed.

SPHERES may also include reporting, recommendations, and action plan functionality. Using multiple data points over time, digital reports may be generated showing progress or decline and items of concern. These snapshot reports may be used to understand the whole picture of a loved one's Independent Living situation. Are they able to live independently? Do they need assistance? Has a fall or injury happened? Are they depressed and staying in bed longer/not eating? Are there cognitive issues? Is medication being taken? Is the medication beneficial or affective? Based upon passive monitoring of routines and behaviors, these and more are questions SPHERES can help a family and professional caregivers understand an independent living environment, make comparisons to progress and decline, and which can inform discussions and decisions for or with a loved one.

SPHERES may also include equipment and devices used to passively monitor a home and/or occupants. A first and primary source monitored may be Electrical Use Monitoring System (such as one that may be tied into, or a part of, a home's main breaker box) may be used to monitor time used, duration, what device is asking for power (e.g., appliance, furnace, hot water heater, devices, garage door, overhead lights/lamp, alarm, electrical outlet, water pump, ignition source), and/or what is providing external power (e.g., generator for emergencies). Other sources monitored may include smart phones, mobile devices, connected devices, connected assistants, connected appliances, connected home controls, connected safety systems, connected lighting or speaker systems, connected robotics or sensors, connected motion sensors, connected water sensors, connected gas and ignition monitors, connected contact sensors, connected air movement/draft sensors, connected pet monitoring, geo locator tags, weather monitor, connected vehicle sensors, Wi-Fi activity, medication dispensers or medical dispenser sensors, 3D printers, nano-bots, fine motor control measurements, and/or smart toilets/drains.

SPHERES may include sensors that may detect and measure video and still pictures, audio and decibel levels, activity and movement, vibration, light, arm/disarm functionality, temperature (body and house), moisture, odor, heart rate, breathing rate, hydration, weight, glucose/ketones levels, medical adherence, travel and location, socialization, medical/health monitor use, appliance and electronics use, air quality, sleep, eye movement, exercise, body control, fine motor control, speech, health, nutrition, hygiene, and/or sight and hearing.

The data collected by SPHERES may be analyzed by one or more artificial intelligence or machine learning models, modules, algorithms, or programs, including the types of machine learning techniques discussed elsewhere herein. For instance, the artificial intelligence or machine learning models, modules, algorithms, or programs may be trained using sample image, audio, home telematics, or other types of data, including video and still images. Once trained, current or near real-time data, including video, image, audio, home telematics, or other data, may be input into trained models, modules, algorithms, or programs to identify abnormal or normal conditions or events, such as presence, walking patterns, falls, hazards, imminent danger, evidence of atypical behavior (physical, mental, emotional, social), intruders, theft, fraud, abuse, detecting position of furniture for safety layout recommendations, detecting trip and/or other hazards. Also detected may be moisture/puddles on the floor or other surfaces or ceiling, and/or when lights are on and off.

Audio and decibel conditions or events may also be identified or detected by artificial intelligence programs or trained machine learning models, modules, programs, or algorithms, such as typical and atypical voice patterns (representing stoke, Alzheimer's detection, hearing decline—increased TV volume, cognitive decline—such as repeating), social (such as decline in conversation or detecting other people in the house), fall detection, behavioral change (such as more aggression, arguing or less conversation than normal), laughter, crying, other sounds relating to emotion, vehicle coming and going.

Activity and movement may also be identified or detected by artificial intelligence programs or trained machine learning models, modules, programs, or algorithms, such as moving from room to room, pace and speed of movement, time spent in a space, time spent outside of the house, atypical movement (such as a seizure or movement before or after a fall or injury), patterned walking style, movements and activities related to cooking, cleaning, exercise, entertainment, social, detecting movements associated with a trip or stumble, and/or eye movement.

Activity and movement may also be identified or detected by artificial intelligence programs or trained machine learning models, modules, programs, or algorithms, such as detecting fall and impact level of fall, detect an item drop/breaking, detecting entry/exit, detecting tornado, earthquake, or other disaster event, phone text/call, and/or a vehicle coming going.

Light switch/light activation may also be identified or detected by artificial intelligence programs or trained machine learning models, modules, programs, or algorithms, such as detecting when lights turn on and off for individual locations, for what amount of time, and date of activation. The sensor or other data collected may also be used to detect activity of automatic lights that activate when movement or other stimulus is detected.

Arming and disarming functionality may also be identified or detected by artificial intelligence programs or trained machine learning models, modules, programs, or algorithms. For instance, conditions that may be identified or detected include entry/exit, alarm activation/disarm, alarm activation with no disarm, number of times over an amount of time, such as hour or single day a home security alarm is armed and disarmed. Also detected may be the amount of accidental alarm activations, and/or the amount of times exiting a home with arming.

Home, home systems, and body temperature may also be identified or detected by artificial intelligence programs or trained machine learning models, modules, programs, or algorithms. For instance, conditions that may be identified or detected include, home temperature highs, lows, and averages; hot water temperature from heater, faucets, and bathtub/showers; oven or stovetop temperatures; body temperature of inhabitants to understand if a notification is needed due to illness, accident, or death; differentiation of temperature between rooms of the house; and/or if vents or windows are open or closed.

Moisture may also be identified or detected by artificial intelligence programs or trained machine learning models, modules, programs, or algorithms. For instance, conditions that may be identified or detected include plumbing or other leaks, sump pump activation/issue, humidity averages and out of average range in the home, and/or bed wetting or accidents.

Odor may also be identified or detected by artificial intelligence programs or trained machine learning models, modules, programs, or algorithms. For instance, conditions that may be identified or detected may include carbon monoxide/dioxide, air quality, smoke, stagnant air, mold/mildew, ammonia, body odor, feces, pet, urine, natural gas, burning food, and/or the presence of certain foods which cause allergic reactions.

Medical/bio data may also be identified or detected by artificial intelligence programs or trained machine learning models, modules, programs, or algorithms. For instance, conditions that may be identified or detected may include medical information or characteristics, such as heart rate, BP, cholesterol, glucose, ketones, weight, hydration, nutrition, medication adherence or non-adherence, medical/health monitor device use/adherence at home, and/or breathing rate.

Travel and location may also be identified or detected by artificial intelligence programs or trained machine learning models, modules, programs, or algorithms. For instance, GPS, travel itinerary, routine locations, mode or service, purchases of travel, airline, train, or Uber, length and time of travel, travel delays, interruptions, and/or difficulties.

Socialization may also be identified or detected by artificial intelligence programs or trained machine learning models, modules, programs, or algorithms. For instance, conditions that may be identified or detected may include interaction routines, who interaction is with, how many times a day/week/month, and/or types/categories of conversations.

Appliance and electronics use may also be identified or detected by artificial intelligence programs or trained machine learning models, modules, programs, or algorithms.

In the event that a condition, event, or abnormal condition is detected or identified, a caregiver may receive a digital notification. For instance, digital messages may be received, such as via a mobile device, for fall, medical, emergency, or critical event, entry/exit, travel, or a list of caregiver selected events for anything outside of norms or recommended norms in the above document.

Digital reports may be generated and transmitted to a caregiver's mobile or other computing device. The digital reports may be easy to scan, read, print, share, and analyze Daily, Weekly, and Yearly snapshot reports; customized time period reports; and/or comparative timeframe reports. The reports may detail the number of notifications sent to caregiver and for what; and/or medication taken, for what, and if that medication is working. The reports may highlight areas of concern, areas of decline, and areas where intervention or improvement needs to take place or needs assistance or additional assistance. The reports may suggest/ recommend actions to be taken, and/or may feature recommended services, support, and resources within a certain proximity of the location. The reports may feature number ranges of optimal (based upon age/ability) levels of physical, mental, social, and emotional engagement, activity, and ability and where recipients of care rank.

The reports may further suggest goals and goal setting/ meeting features and/or provide an Independent Living overall score—as an example for demonstration: 100 representing ideal independent living capability, 70 representing family/support services interaction needed for independent living capability, 60 representing significant family/ support services interaction needed to live independently, and 50 and below representing professional assistance needed. The reports may be able to be shared with doctors and selected family members but secured with a rotating generated password provided by the designated primary family caregiver or Power of Attorney. Additionally or alternatively, the reports may be encrypted using blockchain or similar technology.

Additional Considerations

With the foregoing, an insurance customer may opt-in to a rewards, insurance discount, or other type of program. After the insurance customer provides their affirmative consent, an insurance provider remote server may collect data from the customer's mobile device, smart home controller, smart vehicles, computers, televisions, or other smart devices—such as with the customer's permission or affirmative consent. The data collected may be related to insured assets before (and/or after) an insurance-related event, including those events discussed elsewhere herein. In return, risk averse insureds may receive discounts or insurance cost savings related to home, renters, personal articles, auto, and other types of insurance from the insurance provider.

In one aspect, data, including the types of data discussed elsewhere herein, may be collected or received by an insurance provider remote server, such as via direct or indirect wireless communication or data transmission from a smart home controller, mobile device, or other customer computing device, after a customer affirmatively consents or otherwise opts-in to an insurance discount, reward, or other program. The insurance provider may then analyze the data received with the customer's permission to provide benefits to the customer. As a result, risk averse customers may receive insurance discounts or other insurance cost savings based upon data that reflects low risk behavior and/or technology that mitigates or prevents risk to (i) insured assets, such as homes, personal belongings, or vehicles, and/or (ii) home or apartment occupants.

Although the foregoing text sets forth a detailed description of numerous different embodiments, it should be understood that the legal scope of the invention may be defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that may be permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that may be temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it may be communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within an office environment, or as a server farm), while in other embodiments the processors may be distributed across a number of locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment may be included in at least one embodiment. The appearances of the phrase "in one embodiment" in various places in the specification are not necessarily all referring to the same embodiment.

As used herein, the terms "comprises," "comprising," "may include," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also may include the plural unless it is obvious that it is meant otherwise.

This detailed description is to be construed as examples and does not describe every possible embodiment, as describing every possible embodiment would be impractical, if not impossible. One could implement numerous alternate embodiments, using either current technology or technology developed after the filing date of this application.

Unless a claim element is defined by reciting the word "means" and a function without the recital of any structure, it is not intended that the scope of any claim element be interpreted based upon the application of 35 U.S.C. § 112(f). The systems and methods described herein are directed to an improvement to computer functionality, and improve the functioning of conventional computers.

What is claimed is:

1. A computer-implemented method for training a machine learning module to identify abnormalities or anomalies corresponding to historically identified conditions associated with one or more individuals in a home environment, comprising:
   receiving, by a processor, historical sensor data detected by one or more sensors associated with the home environment;
   identifying, by the processor, one or more abnormalities or anomalies in the historical sensor data;
   receiving, by the processor, historical condition data indicating historically identified conditions associated with one or more individuals in the home environment, wherein the historically identified conditions include one or more of: a medical condition, a health condition, a cognitive condition, a forgetfulness condition, an insomnia condition, a fatigue condition, a hygiene condition, an emergency condition, or an urgent condition;
   analyzing, by the processor, using the machine learning module, the one or more abnormalities or anomalies in the historical sensor data and the historical condition data; and
   identifying, by the processor, using the machine learning module, based upon the analysis, the one or more abnormalities or anomalies in the historical sensor data corresponding to one or more of the historically identified conditions associated with the one or more individuals in the home environment.

2. The computer-implemented method of claim 1, further comprising:
capturing current data detected by one or more sensors associated with a home environment; and
analyzing, by the processor, the captured current data to identify one or more abnormalities or anomalies in the current data using the machine learning module.

3. The computer-implemented method of claim 2, further comprising:
comparing, by the processor, the one or more abnormalities or anomalies in the current data to the abnormalities or anomalies in the historical sensor data corresponding to historically identified conditions associated with the one or more individuals in the home environment; and
determining, by the processor, based upon the comparison, a current condition associated with an individual in the home environment using the machine learning module.

4. The computer-implemented method of claim 3, further comprising:
generating, by the processor, a notification indicating the current condition associated with the individual in the home environment.

5. The computer-implemented method of claim 3, wherein the current condition associated with the individual is a medical condition.

6. The computer-implemented method of claim 3, wherein the current condition associated with the individual is an emergency medical condition, the method further comprising:
requesting, by the processor, based upon the emergency medical condition, an emergency service to be provided to the individual.

7. The computer-implemented method of claim 3, wherein the current condition associated with the individual is a gait of the individual.

8. The computer-implemented method of claim 3, wherein the current condition associated with the individual is whether or not the individual is sleeping.

9. The computer-implemented method of claim 1, wherein the historical sensor data comprising at least one of a body temperature, a heart rate, a breathing rate, a glucose level, a ketone level, medication adherence data, eye movement data, exercise data, body control data, fine motor control data, health data, and nutrition data.

10. The computer-implemented method of claim 1, further comprising:
modifying, by the processor, the machine learning module based upon the analysis and the identified one or more abnormalities or anomalies with corresponding historically identified conditions.

11. The computer-implemented method of claim 1, wherein the one or more sensors associated with the home environment include one or more sensors configured to capture data indicative of electricity use by devices associated with the home environment.

12. The computer-implemented method of claim 11, wherein the data indicative of electricity use includes an indication of at least one of:
which device is using electricity;
a time at which electricity is used by a particular device;
a date at which electricity is used by a particular device;
a duration of electricity use by a particular device; and
a power source for the electricity use.

13. A computer system for training a machine learning module to identify abnormalities or anomalies corresponding to historically identified conditions associated with one or more individuals in a home environment, comprising:
one or more processors; and
one or more non-transitory memories storing computer executable instructions that, when executed by the one or more processors, cause the computer system to:
receive historical sensor data detected by one or more sensors associated with the home environment;
identify one or more abnormalities or anomalies in the historical sensor data;
receive historical condition data indicating historically identified conditions associated with the one or more individuals in the home environment, wherein the historically identified conditions include one or more of: a medical condition, a health condition, a cognitive condition, a forgetfulness condition, an insomnia condition, a fatigue condition, a hygiene condition, an emergency condition, or an urgent condition;
analyze, using the machine learning module, the one or more abnormalities or anomalies in the historical sensor data and the historical condition data; and
identify, using the machine learning module, based upon the analysis, the one or more abnormalities or anomalies in the historical sensor data corresponding to one or more of the historically identified conditions associated with the one or more individuals in the home environment.

14. The computer system of claim 13, wherein the computer executable instructions further cause the computer system to:
capture current data detected by one or more sensors associated with a home environment; and
analyze the captured current data to identify one or more abnormalities or anomalies in the current data using the machine learning module.

15. The computer system of claim 14, wherein the computer executable instructions further cause the computer system to:
compare the one or more abnormalities or anomalies in the current data to the abnormalities or anomalies in the historical sensor data corresponding to historically identified conditions associated with the one or more individuals in the home environment; and
determine, based upon the comparison, a current condition associated with an individual in the home environment using the machine learning module.

16. The computer system of claim 15, wherein the computer executable instructions further cause the computer system to:
generate a notification indicating the current condition associated with the individual in the home environment.

17. The computer system of claim 15, wherein the current condition associated with the individual is a medical condition.

18. The computer system of claim 15, wherein the current condition associated with the individual is an emergency medical condition,
wherein the computer executable instructions further cause the computer system to: request, based upon the emergency medical condition, an emergency service to be provided to the individual.

19. The computer system of claim 13, wherein the one or more sensors associated with the home environment include one or more sensors configured to capture data indicative of electricity use by devices associated with the home environment.

20. The computer system of claim 19, wherein the data indicative of electricity use includes an indication of at least one of:
   which device is using electricity;
   a time at which electricity is used by a particular device;
   a date at which electricity is used by a particular device;
   a duration of electricity use by a particular device; and
   a power source for the electricity use.

21. The computer system of claim 13, wherein the historical sensor data comprising at least one of a body temperature, a heart rate, a breathing rate, a glucose level, a ketone level, medication adherence data, eye movement data, exercise data, body control data, fine motor control data, health data, and nutrition data.

22. The computer system of claim 13, wherein the computer executable instructions further cause the computer system to:
   modify the machine learning module based upon the analysis and the identified one or more abnormalities or anomalies with the corresponding historically identified conditions.

23. The computer system of claim 13, wherein the computer executable instructions further cause the computer system to interact with a voice-activated assistant.

* * * * *